US006183984B1

(12) United States Patent
Fuchs

(10) Patent No.: US 6,183,984 B1
(45) Date of Patent: Feb. 6, 2001

(54) SEQUENCES FOR PROMOTING EPIDERMAL CELL-SPECIFIC TRANSCRIPTION

(75) Inventor: Elaine V. Fuchs, Chicago, IL (US)

(73) Assignee: Arch Development Corporation, Chicato, IL (US)

( * ) Notice: Under 35 U.S.C. 154(b), the term of this patent shall be extended for 0 days.

(21) Appl. No.: 07/875,790

(22) Filed: Apr. 29, 1992

Related U.S. Application Data

(63) Continuation-in-part of application No. 07/791,664, filed on Nov. 12, 1991, now abandoned.
(51) Int. Cl.$^7$ .......................... C07H 21/04; C12P 21/00; C12N 15/85; C12N 5/10
(52) U.S. Cl. .................. 435/69.1; 435/172.3; 435/320.1; 435/325; 435/371; 536/24.1
(58) Field of Search ................. 536/23.1, 24.1; 435/69.1, 320.1, 172.3, 252.3, 325, 371, 357

(56) References Cited

U.S. PATENT DOCUMENTS 4,935,363   6/1990   Brown et al. ..................... 435/172.3

OTHER PUBLICATIONS

Jiang et al. (1990) Nuc. Acid Res vol. 18(2): 247–253.*
Muscat et al. (1987) Mol. Cell Biol. vol. 7(11):4089–4099.*
Snape et al. (1990) Development. vol. 109: 157–165.*
Xu et al. (1984) Nature vol. 309:806–810.*
Vassar & Fuchs, "Transgenic Mice Provide New Insights into the Role of TGF–α During Epidermal Development and Differentiation," *Genes & Development*, 5:714–727, 1991.
Vassar et al., "Mutant Keratin Expression in Transgenic Mice Causes Marked Abnormalities Resembling a Human Genetic Skin Disease," *Cell*, 64:365–380, 1991.
Fuchs, J., "Epidermal Differentiation: The Bare Essentials," *Journal of Cell Biology*, 111(6,2):2807–2814, 1990.
Leask et al., "Regulation of a Human Epidermal Keratin Gene: Sequences and Nuclear Factors Involved in Keratinocyte–Specific Transcription," *Genes & Development*, 4:1985–1998, 1990.
Vassar et al., "Tissue–Specific and Differentiation–Specific Expression of a Human K14 Gene in Transgenic Mice," *Proceedings of the National Academy of Sciences, USA*, 86:1563–1567, 1989.
Leask et al., "Transcription Factor AP2 and its Role in Epidermal–Specific Gene Expression," *Proceedings of the National Academy of Sciences, USA*, 88:7948–7952, 1991.
Aneskievich, Letai, and Fuchs, Epidermal Keratinocytes: Opportunities and Applications in Somatic Cell Gene Therapy, In *Somatic Gene Therapy*, pp. 73–90, Edited by Chang, P.L., CRC Press, Boca Raton, 1995.

Byrne and Fuchs, "Probing Keratinocyte and Differentiation Specificity of the Human K5 Promoter In Vitro and in Transgenic Mice," *Molecular and Cellular Biology*, 13(6):3176–3190, Jun. 1993.
Byrne, Tainsky, and Fuchs, "Programming Gene Expression in Developing Epidermis," *Development*, 120:2369–2383, 1994.
Cheng et al., "Cachexia and Graft–vs.–Host–Disease–Type Skin Changes in Keratin Promoter–Driven TNFα Transgenic Mice," *Genes & Development*, 6:1444–1456, 1992.
Fuchs, E., "Epidermal Differentiation and Kertin Gene Expression," *Journal of Cell Science*, Supplement 17:197–208, 1993.
Fuchs, Esteves, and Coulombe, "Transgenic Mice Expressing a Mutant Keratin 10 Gene Reveal the Likely Genetic Basis for Epidermolytic Hyperkeratosis," *Proc. Natl. Acad. Sci. USA*, 89:6906–6910, Aug. 1992.
Guo, Yu, and Fuchs, "Targeting Expression of Keratinocyte Growth Factor to Keratinocytes Elicits Striking Changes in Epithelial Differentiation in Transgenic Mice," *The EMBO Journal*, 12(3):973–986, 1993.
Leff, D.N., "Murine Skin–Cell Promoters, As DNA Vectors, Ferry Human Hormone Genes Into Mice," *Bio World Today: The Daily Biotechnology Newspaper*, 8(6):1 and 3, Jan. 9, 1997.
Turksen et al., "Interleukin 6: Insights to Its Function in Skin by Overexpression in Transgenic Mice," *Proc. Natl. Acad. Sci. USA*, 89:5068–5072, Jun. 1992.

* cited by examiner

*Primary Examiner*—David Guzo
(74) *Attorney, Agent, or Firm*—Arnold White & Durkee

(57) ABSTRACT

The present disclosure provides a detailed characterization of the sequences and factors controlling expression of a human gene expressed specifically in keratinocytes. Using 5' upstream sequence of the human K14 keratin gene coupled to one of two reporter genes, sequences necessary and sufficient for expression of K14 have been examined in both cultured human keratinocytes and in mitotically active basal keratinocytes of transgenic mouse epidermis. The existence of distal and proximal elements located 5' from the transcription initiation site of the hK14 gene is demonstrated, which when combined with a TATA box element, appear to act in concert to drive keratinocyte-specific expression. The proximal element was also examined. After using CAT assays to narrow the transcriptional activation element to within 110 bp, the existence of a keratinocyte nuclear factor was determined, termed KER1 (AP2), which binds to the 10 bp palindromic sequence, 5' G C C T G C A G G C 3', within this domain. The data suggest that both the sequence and the nuclear factor that has been identified are involved, in conjunction with a distal element (−1700 to −2100 of the human K14 gene) in controlling keratinocyte-specific expression in vitro and in vivo.

17 Claims, 16 Drawing Sheets

| COMPETITORS | | | |
|---|---|---|---|
| NO. | NAME | | SEQUENCE |
| 1 | K14wt | -242 | GTGGAAAGTGTAGCCTGCAGGCCCACACCTCCCCCTGTAATCACGCCG -196 |
| 2 | K14mut | -242 | GTGGAAAGTGTATAGGATCCACCCACACCTCCCCCTGTAATCACGCCG -196 |
| 3 | K14mut (-231) | -242 | GTGGAAAGTGTATCCTGCAGGCCCACACCTCCCCCTGTAATCACGCCG -196 |
| 4 | K14mut (-230) | -242 | GTGGAAAGTGTAGACTGCAGGCCCACACCTCCCCCTGTAATCACGCCG -196 |
| 5 | K14mut (-229) | -242 | GTGGAAAGTGTAGCATGCAGGCCCACACCTCCCCCTGTAATCACGCCG -196 |
| 6 | K14mut (CEII) | -242 | GTGGAAAGTGTAGCCTGCAGGCAGCTACCTCCCCCTGTAATCACGCCG -196 |
| 7 | HPV(CEII) | 5' | TGCCAACAACACCTGGCGCGGGTATTGC 3' |
| 8 | K14 (CK8mer) | -195 | TGGCGGGACAAGAAAGCCCAAACACTCCAAACAATG -159 |
| 9 | K1 | -138 | CGTAAAAATCTTGTATGGCTGCAGGAAGCCAAACCCTTGAC -96 |

FIG. 9A

SEQUENCES FOR PROMOTING EPIDERMAL CELL-SPECIFIC TRANSCRIPTION

The present application is a continuation-in-part of U.S. Ser. No. 07/791,664, filed Nov. 12, 1991 now abandoned.

The Government may own certain rights in the present invention pursuant to NIH grant AR31737.

BACKGROUND OF THE INVENTION

1. Field of the Invention

The present invention relates to sequences useful in the control of gene expression and, in particular, to sequences for promoting keratinocyte-specific gene expression.

2. Description of the Related Art

Keratinocytes are cells found exclusively in stratified squamous epithelia, including epidermis, tongue, esophagus, cervix and cornea (for review, see Watt, 1988). As surface and lining cells, keratinocytes have several unusual structural features in common, including (a) 10 nm keratin intermediate filaments (IFs), which constitute a major part of the keratinocyte cytoskeleton, (b) desmosomes, which are membranous plaques responsible for interconnecting keratinocytes as a cellular sheet, and (c) a group of inner membrane envelope proteins, which become covalently cross-linked by transglutaminase when keratinocytes undergo terminal differentiation. In addition, differentiating keratinocytes are the natural cell type-specific hosts for a family of circular, double-stranded DNA viruses known as papillomaviruses, although expression of HPV genes has also been detected in relatively undifferentiated cervical carcinomas in vivo as well as simple epithelial-like cervical carcinoma cells in vitro (for a review, see Broker and Botchan, 1986).

Despite minor differences, mitotically active keratinocytes from different stratified squamous epithelial tissues appear to be quite similar not only in morphology but also in biochemistry (Nelson and Sun, 1983). The major proteins expressed by these cells are a pair of keratins, K5 (58 kd) and K14 (5 kd), which form the 10 nm cytoskeletal filaments (Nelson and Sun, 1983; Eichner et al., 1986). In differentiating keratinocytes, the major proteins are also keratins, but in this case, the keratins are expressed in a tissue-specific fashion (for reviews, see Moll et al., 1982; Sun et al., 1984). For epidermis, terminally differentiating cells in vivo express keratins K1 (67 kd) and K10 (56.5 kd) (Fuchs and Green, 1980; Moll et al., 1982; Roop et al., 1983), and suprabasal cells in vitro express K6 (56 kd) and K16 (48 kd) (Kopan and Fuchs, 1989).

Little is known about the molecular mechanisms underlying the expression of genes in basal keratinocytes or the processes controlling changes in keratin and viral gene expression during keratinocyte differentiation. However, a number of recent studies have begun to focus on identifying putative regulatory domains and transcription factors which might be involved in expression of either endogenous or viral genes in keratinocytes (Marchuk et al., 1985; Blessing et al., 1987; 1989; Cripe et al., 1987; Hirochika et al., 1988; Vassar et al., 1989; Chin et al., 1989; Jiang et al., 1990). For papillomaviruses, assessing the relevance to keratinocyte-specific gene expression has been complicated because (a) the viral genomes encode proteins which influence transcription of viral genes and (b) even though HPV genes are preferentially expressed in keratinocytes in vivo, most in vitro studies have been carried out with HeLa or C-33A cells, both of which appear to be relatively undifferentiated, simple epithelial-like cervical carcinoma cells that do not express most keratinocyte-specific structural proteins.

Given this caveat, several HPV genes have been shown to contain sequences (defined to limits as small as ~30–100 bp) which are not only required for viral expression but also bind epithelial-specific proteins (Cripe et al., 1987; Swift et al., 1987; Gloss et al., 1987; Hirochika et al., 1988; Gius et al., 1988; Chin et al., 1989). In contrast, for genes expressed naturally in keratinocytes, only coarsely defined regulatory domains (300 bp or greater) have thus far been identified (Vassar et al., 1989; Blessing et al., 1989; Jiang et al., 1990).

In the absence of molecular studies, the 5' upstream sequences of a number of genes expressed specifically in keratinocytes have been screened for similarities which might provide clues as to sequences which might be important for gene expression (Marchuk et al., 1985; Tyner et al., 1985; Johnson et al., 1985; Blessing et al., 1987; Lersch et al., 1989). From these comparisons, several putative regulatory sequences have been postulated based upon either extensive similarities to known viral enhancer sequences, e.g. the SV40 core enhancer (Marchuk et al., 1985), the widespread occurrence of a sequence, e.g. the CK 8-mer consensus sequence 5' A A N C C A A A 3' (Blessing et al., 1987; Cripe et al., 1987), or the conservation of a sequence, e.g. 5' T G C A G G T G T G A 3' (SEQ ID NO:2) among two closely related genes (Lersch et al., 1989).

Since so little is known about the sequences and transcription factors involved in keratinocyte-specific expression, the extent to which such comparisons will prove to be valid is almost wholly unknown. Among the questions which remain to be answered are: Is there a common regulatory mechanism controlling expression of a large number of keratinocyte-specific genes? Are papillomavirus and keratinocyte genes regulated in similar fashions? Are the same transcription factors recruited to control gene expression in dividing and differentiating keratinocytes? Clearly, elucidating sequences necessary for keratinocyte-specific gene expression and purification of the proteins which interact with these sequences is a prerequisite to understanding transcription of genes in keratinocytes. To begin to investigate cell type-specific expression in keratinocytes, the functional human genes encoding K14 have been isolated and characterized (Marchuk et al., 1985) and K5 (Lersch et al., 1989). Not only do these genes encode the major keratinocyte proteins, but in embryogenesis, their expression is upregulated coincident with the commitment of an embryonic basal cell to an epidermal fate (Kopan and Fuchs, 1989).

Previously, it has been reported that a human K14 gene construct containing ~2300 bp of 5' upstream sequence gave specific expression in the basal layers of stratified squamous epithelia in transgenic mice (Vassar et al., 1989). However, this previous study failed to identify the specific regions or nucleotide sequences that might be responsible for conferring specific expression. Therefore, this information does not allow one the ability to multimerize and/or employ smaller sequences and factors that play a role in mediating epithelial-specific expression. These smaller, specific sequences could be used to confer specific expression without resort to the 2300 bp sequence reported by Vassar et al. In addition, multimerization of these sequences might be used to create more powerful expression without loss of tissue specificity. Accordingly, there is a continuing need for the identification of the precise sequences controlling epithelial-specific gene expression. Moreover, there is a need for the identification of the actual stretches of nucleotides responsible for mediating the specificity, as well as a need for the development of control regions having an improved mediating capability.

SUMMARY OF THE INVENTION

In its most general and overall scope, the present invention is directed to DNA segments which, when located upstream from and proximal to a transcription initiation site of a selected structural gene, serve to confer a keratinocyte specific, and often epidermal abundant, expression capability to such a gene. These DNA segments have been identified and constructed from a consideration and manipulation of DNA sequences found in the gene regions upstream of keratinocyte-specific genes, such as used herein, the term "upstream" refers to DNA sequences found in a 5' direction from a given point of reference along a DNA molecule.

Most importantly and surprisingly, it has been found that the keratinocyte specific control elements of the present invention are functionally translocatable to other structural genes. Thus, when these elements are located upstream of a selected heterologous structural gene, keratinocyte-specific regulation is conferred to this "hybrid" gene. Therefore, as used herein, the term "functionally translocatable" refers to genetic elements which retain their functional capability in contexts other than their natural state, and the term "hybrid" gene refers to a man-made gene constructed through the application of recombinant DNA techniques to bring together genetic elements not normally associated in nature. Moreover, the term "heterologous structural gene" refers to structural genes other than the naturally-associated gene, and the term "structural gene" refers to any DNA segment which may be both transcribed and translated by a cell.

Accordingly, in a general sense, the invention is directed to purified segments of DNA comprising functionally translocatable keratinocyte transcription elements capable of conferring regulation of structural gene transcription to a selected heterologous structural gene when located upstream from and proximal to a transcription initiation site of such a gene, generally provided that said segment is free of the structural gene ordinarily under the transcriptional control of said proximal and distal element sequences.

The proximal element can be defined as including a nucleotide sequence comprising:

5'-G-C-C-T-G-C-A-G-G-C-3' (SEQ ID NO:1)

or the complement of such a sequence. To confer keratinocyte specificity, proximal elements including such sequences must be combined both with a distal element and a TATA box.

Generally, it is proposed that sequence stretches of on the order of 10 to 1500, more preferably 10 to 1000, and still more preferably 10 to 100 nucleotides in length, which incorporate the foregoing proximal, distal and TATA box elements, will be preferred for conferring keratinocyte-specific regulation. In fact, the inventor proposes that even shorter segments of the proximal element, on the order of 10 to 30 nucleotides in length, may be used for conferring such control in combination with the other elements.

In further aspects, the present invention relates to discreet DNA segments represented by the formula:

Distal Element-(X)$_n$-TATA wherein TATA is a TATA box sequence; n≧1; and each X is:

5'-G-C-C-T-G-C-A-G-G-C-3' (SEQ ID NO:1)

and with each X unit, if more than one, being separated by from 0–200 nucleotides selected from the group of nucleotides consisting of A, G, C and T.

The distal region of the keratinocyte transcriptional element of the present invention operates in conjunction with the proximal element palindrome, G-C-C-T-G-C-A-G-G-C (SEQ ID NO:1), to confer keratinocyte specific gene expression. The distal element comprises 300–400 nucleotides from a region located approximately 1700 to 2100 nucleotides upstream from the transcriptional start site, i.e. the −1700 to −2100 nucleotides, of the human K14 gene.

To obtain a DNA sequence containing the distal element, one would simply prepare a DNA segment comprising the nucleotides in the region located 1700 to 2100 nucleotides upstream from the transcriptional start site of the human K14 gene, i.e. nucleotides between −1700 and −2100. This can be achieved, for example, by employing restriction enzymes to excise an appropriate piece of DNA. Any one, or two, of an extensive range of restriction enzymes could be chosen following an analysis of the sequences around broadly around −1700 and −2100 to determine the existence of appropriate restriction sites. If desired, for example, for subsequent ligation strategies, one could even create a particular restriction site by genetic engineering. The use of such restriction enzymes to excise a portion of DNA will be generally known to those of skill in the art in light of the present disclosure.

It is proposed that the distal and proximal sequences of the present invention may confer a regulatory capability regardless of their orientation with respect to the transcribed strand of DNA. Moreover, it is proposed that there may not necessarily be a requirement that these sequences be placed in a particular position with respect to the site of transcription initiation. Thus, they may act in a fashion similar to enhancer elements in this regard.

It is also proposed that the elements may be introduced into a heterologous gene in multiple copies, either in a forward or reversed orientation, and perhaps obtain a much improved regulatory capability. Moreover, multiple units need not be placed in an adjacent conformation and may be separated by numerous random nucleotides and still retain their improved regulatory and promotion capability.

As noted, regulatory elements are advantageously employed by locating said sequences upstream from and proximal to a transcription initiation site of a selected heterologous structural gene. Depending on the particular structural gene employed, these control elements may provide some benefit when located up to 300 nucleotides upstream of a transcription initiation site, as measured from the 3' end of the control sequence.

However, in a preferred embodiment, the sequences are located within 250 nucleotides of transcription initiation.

It is contemplated that the control sequences will prove useful in the context of a wide array of genes which have been characterized to date. Although, as disclosed in more detail below, it is believed that the sequences will prove useful in the context of virtually any structural gene, it is further believed that these sequences will be of particular benefit in the context of human and related structural genes such as the genes for TGFA and other growth factors, EGFR and other growth factor receptors, p53 and other tumor suppressor genes, interferon, lymphokines such as interleukins I, VI and VIII, tumor necrosis factor, and numerous other genes as disclosed herein.

It is an additional object of the present invention to provide control sequences which may be combined with known promoters to provide novel hybrid eukaryotic promoters having regulatory capabilities. Such hybrid promoters may also be employed in the context of selected heterologous structural genes.

It is, therefore, a particular object of the invention to provide a DNA molecule which has incorporated within its structure one or more of the DNA sequences or segments having distal and proximal regulatory elements such as described above, in combination with a structural gene not ordinarily under the transcriptional control of said elements, said structural gene and regulatory elements being combined in a manner such that said structural gene is under the transcriptional control of said regulatory elements.

However, in certain embodiments, the invention will not be limited to use with heterologous structural genes. The present disclosure, thus, additionally provides a method for keratinocyte regulation of expression of a polypeptide in recombinant cell culture or in transgenic animals. These methods both include the following initial steps of:

(a) preparing a first DNA segment which includes the proximal regulatory elements as described above;

(b) constructing a second DNA segment from said first DNA segment by positioning thereon 1 or more copies of said first DNA segment upstream from and proximal to a transcription initiation site of a selected structural gene such that said structural gene may be brought under the transcriptional control of the regulatory element of said first DNA segment; and (c) constructing a third DNA segment from said first DNA segment by positioning thereon one or more copies of the distal regulatory element as described above (−2100 to −1700) upstream from and proximal to the second DNA segment.

Of course, the order of construction of a DNA segment which contains these control elements is not of particular importance, so long as it ultimately includes the proximal and distal elements positioned upstream of the selected structural gene. Once constructed, a third DNA segment such as described above can then be employed to regulate the expression of said selected structural gene either in recombinant cell culture or in transgenic animals, by employing the following steps:

(d) transforming a host cell with said third DNA segment and culturing the transformed host cell to regulate the transcription of said structural gene; or (e) microinjecting a fertilized embryo with said third DNA segment and implanting the injected embryo into the oviduct of a foster mother to produce a transgenic animal in which the transcription of said structural gene is regulated.

In important and further embodiments, a method is provided for determining the ability of a candidate substance to modulate the transcription of keratinocyte specific genes, which method comprises (a) providing a nucleic acid sequence containing the distal and proximal regulatory elements, a promoter and a reporter gene under the transcriptional control of both of the regulatory elements and the promoter which is capable of conferring a detectable signal on a host cell, (b) transfecting said nucleic acid sequence into a host cell to produce a cell culture or transgenic animal, (c) contacting the cell culture or transgenic animal with the candidate substance, and (d) detecting the signal produced by said cell culture or transgenic animal. The greater the signal the greater the activating character of the candidate, or, alternatively, the less the signal, the less the activating character of the candidate. Transcriptionally modulating candidate substances are then evaluated further for potential as, for example, pharmaceutical agents using conventional techniques and animal models.

Constructions of pK14P(−2300) and derivatives are described in the methods section of Example I. Components are from left to right: thick black line, 5' upstream sequence of the human K14 gene (Marchuk et al., 1985) extending from the translation initiation site (+64) to a restriction endonuclease or Bal 31 deletion site located at X kb 5' to this site, where for each plasmid, the distance X is indicated in nucleotides in parentheses; open box, complete coding sequence of human K14 CDNA, and for gene-CDNA hybrids, this region also contains up to 5 of the 7 introns of the human K14 gene (introns are indicated by internal, smaller black boxes); stippled box, sequence coding for substance P tag (Albers and Fuchs, 1987); vertical striped box, K14 3' untranslated sequence extending from 21 bp 3' to the TGA stop codon to the polyadenylation signal (pA); diagonal striped box, K14 gene sequence extending ~700 bp 3' from pA. Abbreviations for restriction endonuclease sites are: R, EcoRI; H3, HindIII; A, AvaI; S, StuI; R5, EcoRV; K, KpnI; Sc, SacII; Bg, BglII; Sp, SphI; H, HaeII. Nomenclature for plasmid names are: p, pGEM plasmid; g, any construct prepared with a K14 gene/cDNA hybrid containing all K14 exons and the first five introns of the K14 gene; K14P, the P-tagged K14; I, any construct prepared with a K14 gene/cDNA hybrid containing all K14 exons and only intron I; V, any construct prepared with a K14 gene/cDNA hybrid containing all K14 exons and only intron V; (−X), the number of 5' upstream K14 nucleotides as described above.

Figure 1A:
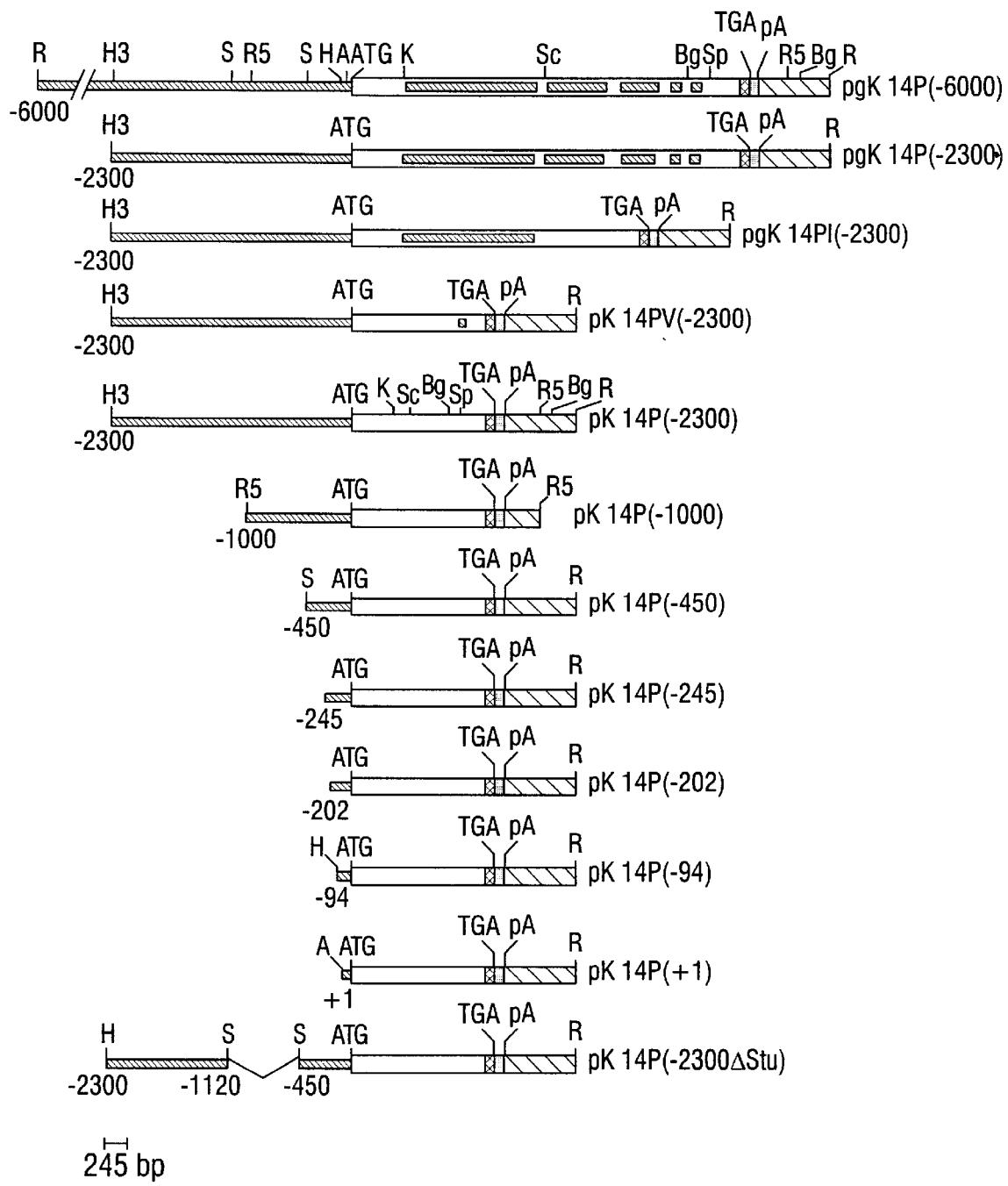
FIG. 1A. Genetic maps of pK14P(−2300) and Derivatives.
Figure 1B:
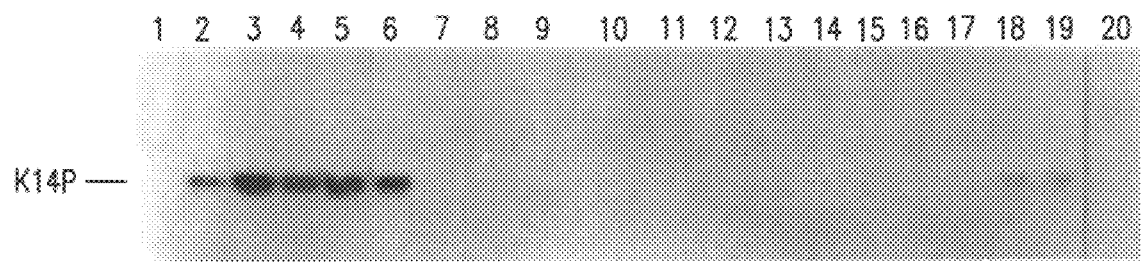

FIG. 1B. Expression of pK14P Constructs in Transiently Transfected SCC-13 Keratinocytes.

SCC-13 cells were transiently transfected with pK14P constructs illustrated in FIG. 1A. At 90 hrs post transfection, cells were lysed and separated into soluble and insoluble fractions. The soluble fraction was removed for β-galactosidase assays to adjust samples for variation in transfection efficiencies, which varied from 0.1–2.0%. The IF proteins were isolated from the insoluble fraction and samples from equal numbers of transfected cells were resolved by SDS polyacrylamide gel electrophoresis (SDS/PAGE) and subjected to immunoblot analysis as described in the methods section of Example I. Lanes represent IF extracts from cells transfected with: lane 1, untransfected; lane 2, pgK14P(−6000); lane 3, pgK14P(−2300); lane 4, pK14PI(−2300); lane 5, pK14PV(−2300); lane 6, pK14P(−2300); lane 7, pK14P(−1000); lane 8, pK14P(−450); lane 9, pgK14P(−450); lane 10, pK14P(−245); lane 11, pgK14P(−245); lane 12, pK14P(−202); lane 13, pgK14P(−202); lane 14, pK14P(−94); lane 15, pgK14P(−94); lane 16, pK14P(+1); lane 17, pgK14P(+1); lane 18, pK14P(−2300ΔStu); lane 19, pgK14P(−2300ΔStu); lane 20, β-galactosidase control plasmid alone. The band detected with anti-P corresponded to the expected mobility of the K14P transgene protein and is indicated at left. Note: Untransfected control cells and cells transfected with 5' deletion constructs containing fewer than 2100 bp upstream sequence showed no K14P protein, even when immunoblots were overexposed for 4 days. Note also that a construct missing the 670 bp internal StuI fragment within the 2300 bp 5' upstream sequence retained its ability to express K14P.

FIG. 2A, FIG. 2B, FIG. 2C, FIG. 2D and FIG. 2E. Tissue-specific Expression of K14P in Transgenic Mice.

Figure 2A:
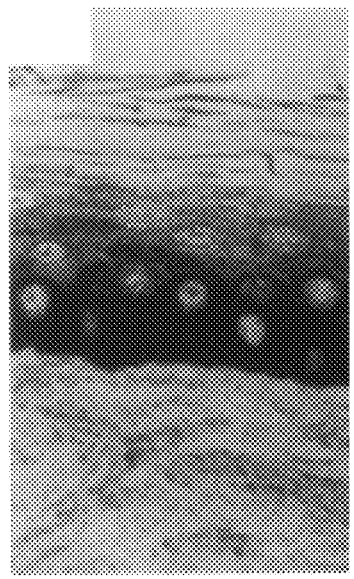
Figure 2B:
Figure 2C:
Figure 2D:
Figure 2E:
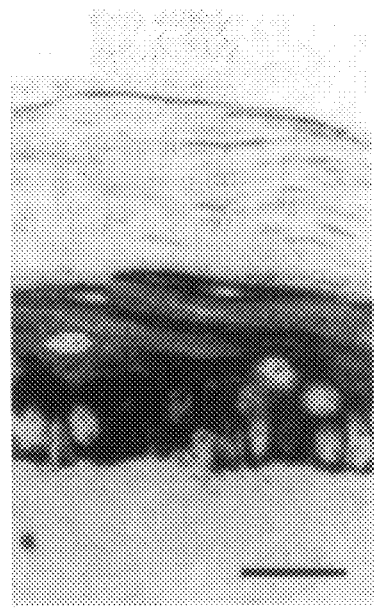

Mouse embryos were microinjected with K14P genes purified from either: pK14P(−2300), containing the entire K14 5' upstream sequence; pK14P(−450), containing the proximal element only; or pK14P(-2300ΔStu), missing 670 bp of 5' upstream sequence, but still containing the K14 proximal and distal elements (see Methods). Transgenic mice were derived and assayed by Southern Blot analyses to determine relative transgene copy number, as described by Vassar et al.(1989). Six different founder mice were obtained for the K14P(-2300) construct, seven for the K14P(-450) construct, and one for the K14P(-2300ΔStu) construct. For all founder mice of a single construct, patterns of transgene expression were similar. Expression in founder mice was examined by immunohistochemistry of Bouin's fixed sections (5 μm) of tail skin. Tails were from: FIG. 2A, transgenic with ~1-2 copies of K14P(-2300); FIG. 2B, negative control mouse; FIG. 2C, transgenic with ~10 copies of K14P(-450); FIG. 2D, transgenic with ~1-2 copies of K14P(-2300ΔStu) showing basal-preferred staining; FIG. 2E, same transgenic in FIG. 2D, but showing some aberrant staining in suprabasal cells. Bar represents 16 μm. Note: none of the K14P(-450) founders showed any evidence of K14P expression.

Figure 3A:
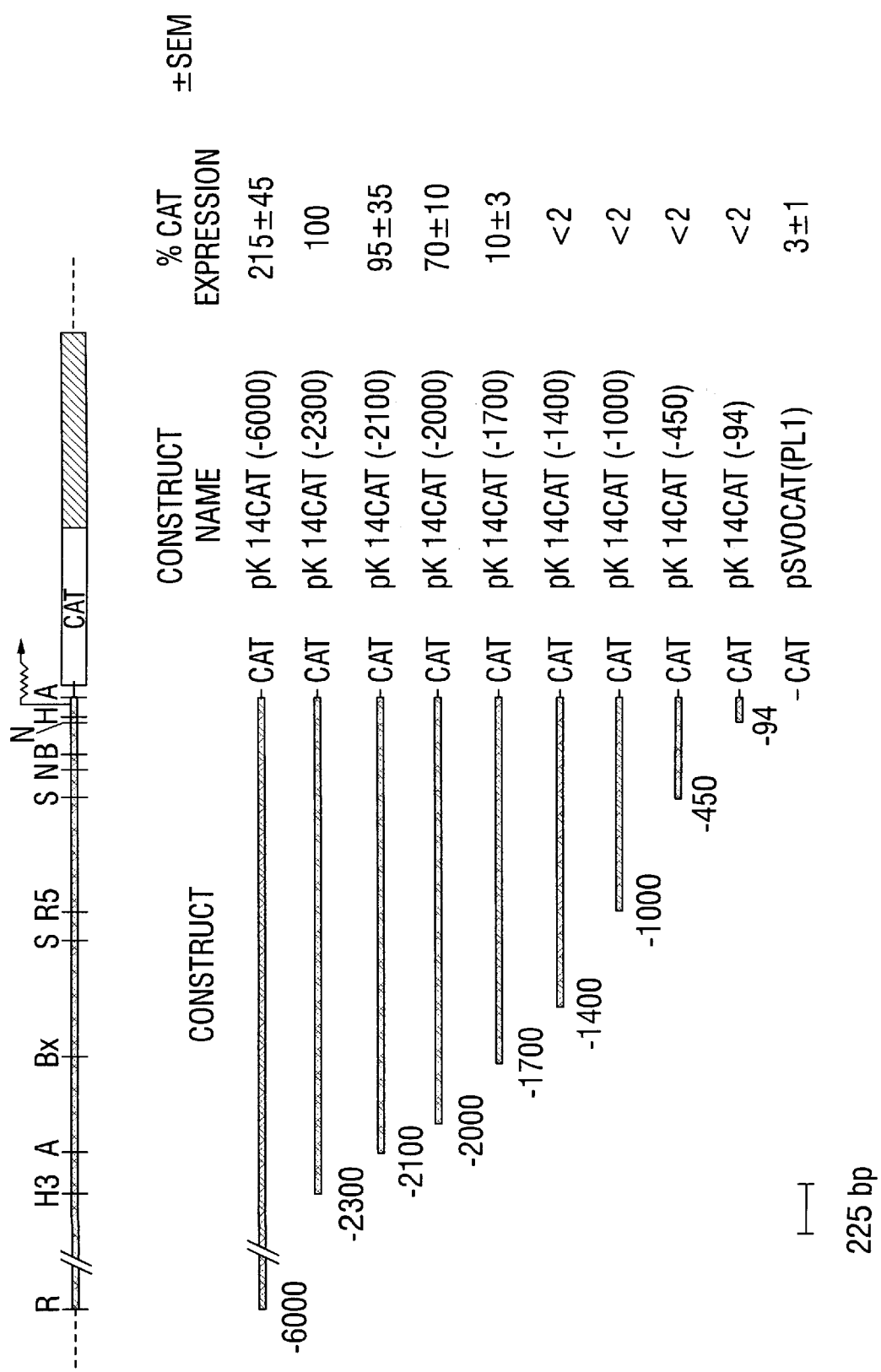
Figure 3B:
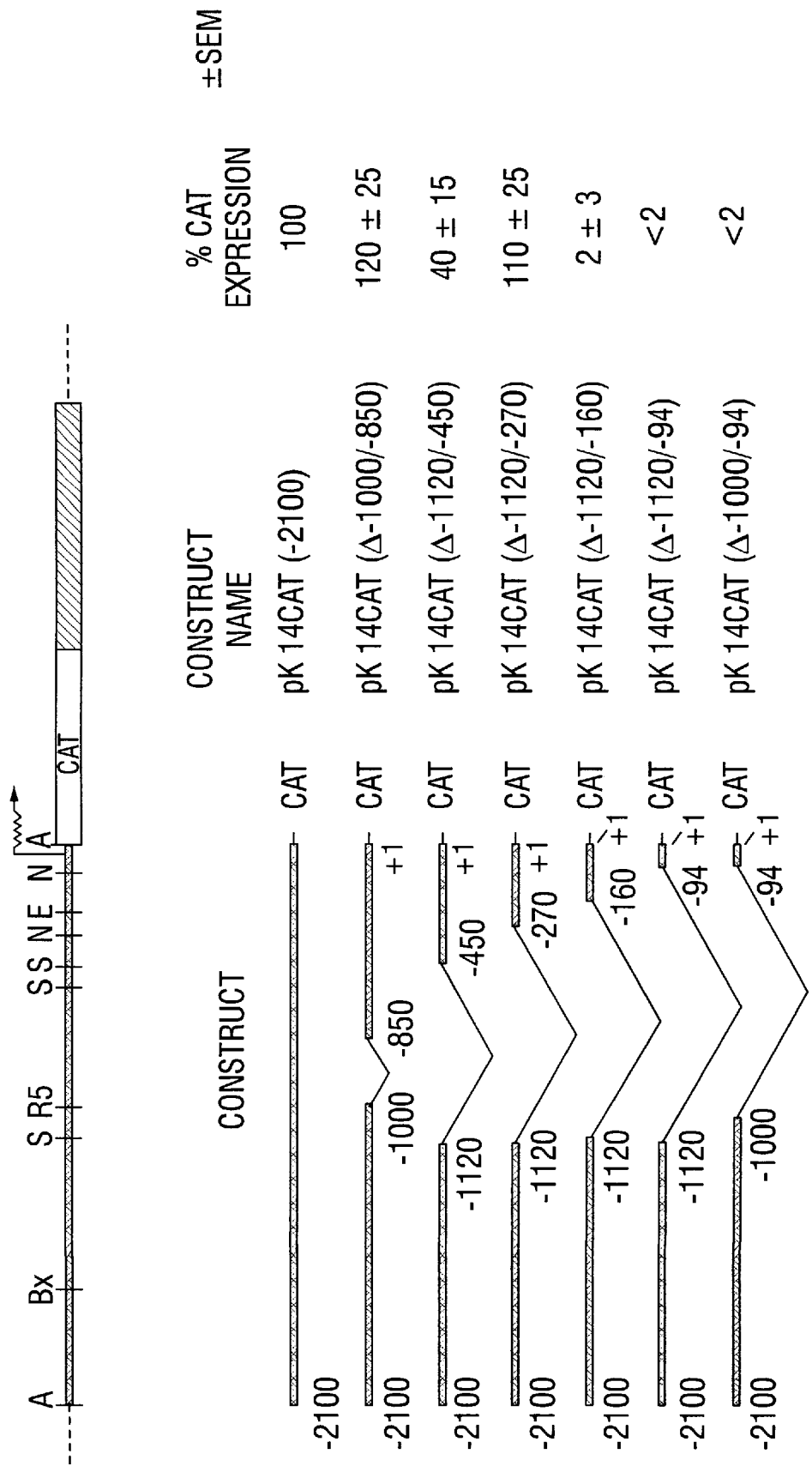

FIG. 3A and FIG. 3B. Genetic maps of pK14CAT Mutants and Expression in Transfected SCC 13 Keratinocytes.

For FIG. 3A and FIG. 3B, constructs are shown at left, and relative CAT values are shown at right. Constructions of pK4CAT(-2300) and derivatives are described in the methods section of Example I. The nucleotide of each 5' boundary of upstream K14 gene sequence is indicated in parentheses, with numbers relative to the transcription initiation site (+1). Components of plasmids are: dotted lines, PBR322 sequences; thin lines, pGEM3 polylinker; thick line, 5' upstream sequence of human K14 gene (Marchuk et al., 1985) extending from the transcription initiation site to a restriction endonuclease or Bal 31 deletion site located at X kb 5' to this site, where for each plasmid, the distance X is indicated in nucleotides in parentheses; open box, complete coding sequence of bacterial chloramphenicol acetyl transferase cDNA; diagonal striped box, SV40 3' noncoding sequence, intron, and polyadenylation signal (Gorman et al., 1983). Transcription initiation site is indicated by squiggly arrow. Abbreviations for restriction endonuclease sites are: R, EcoRI; H3, HindIII; A, AvaI; S, StuI; R5, EcoRV; N, NheI; Bx, BstXI; E, Exonuclease III; B, Bsu36I; H, HaeII. FIG. 3A. The distal element. Each plasmid was co-transfected with a β-galactosidase control gene into SCC-13 keratinocytes, and cell extracts were subsequently assayed for CAT activity and β-galactosidase activity as described in the methods section of example I. CAT activity of each extract was normalized against the control, and is expressed as a percentage of pK14CAT(-2300). FIG. 3B. The proximal element. Each plasmid was co-transfected with a β-galactosidase control gene into SCC-13 keratinocytes, and cell extracts were subsequently assayed for CAT activity and β-galactosidase activity as described above. CAT activity of each extract was normalized against the control, and is expressed as a percentage of pK14CAT (-2100).

Figure 4:
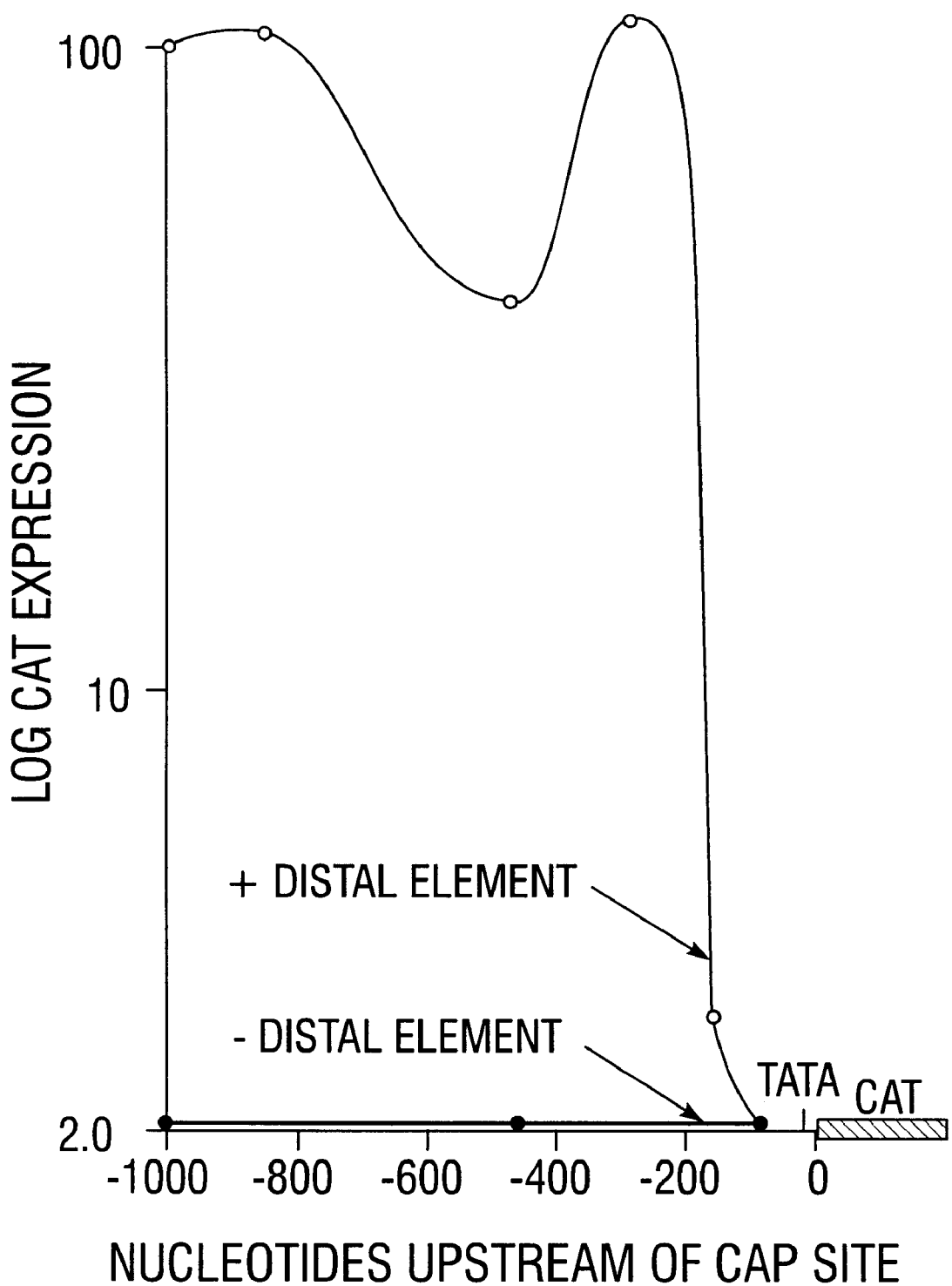

FIG. 4. Schematic Representation of Cooperativity Between Distal and Proximal Elements of the K14 Gene.

This graph shows the CAT expression levels of different K14 promoter deletion constructs with (o) or without (.) the distal promoter element. Deletions start at -1000 and progress toward the TATA box, with (-x) representing the number of 5' upstream K14 nucleotides. CAT data, taken from FIG. 3A and FIG. 3B, are expressed as a percentage of pK14(-2100). Any CAT value below 2% was assumed to be below the levels of detectability of the assay, and is entered on the graph as being 2%.

Figure 5:
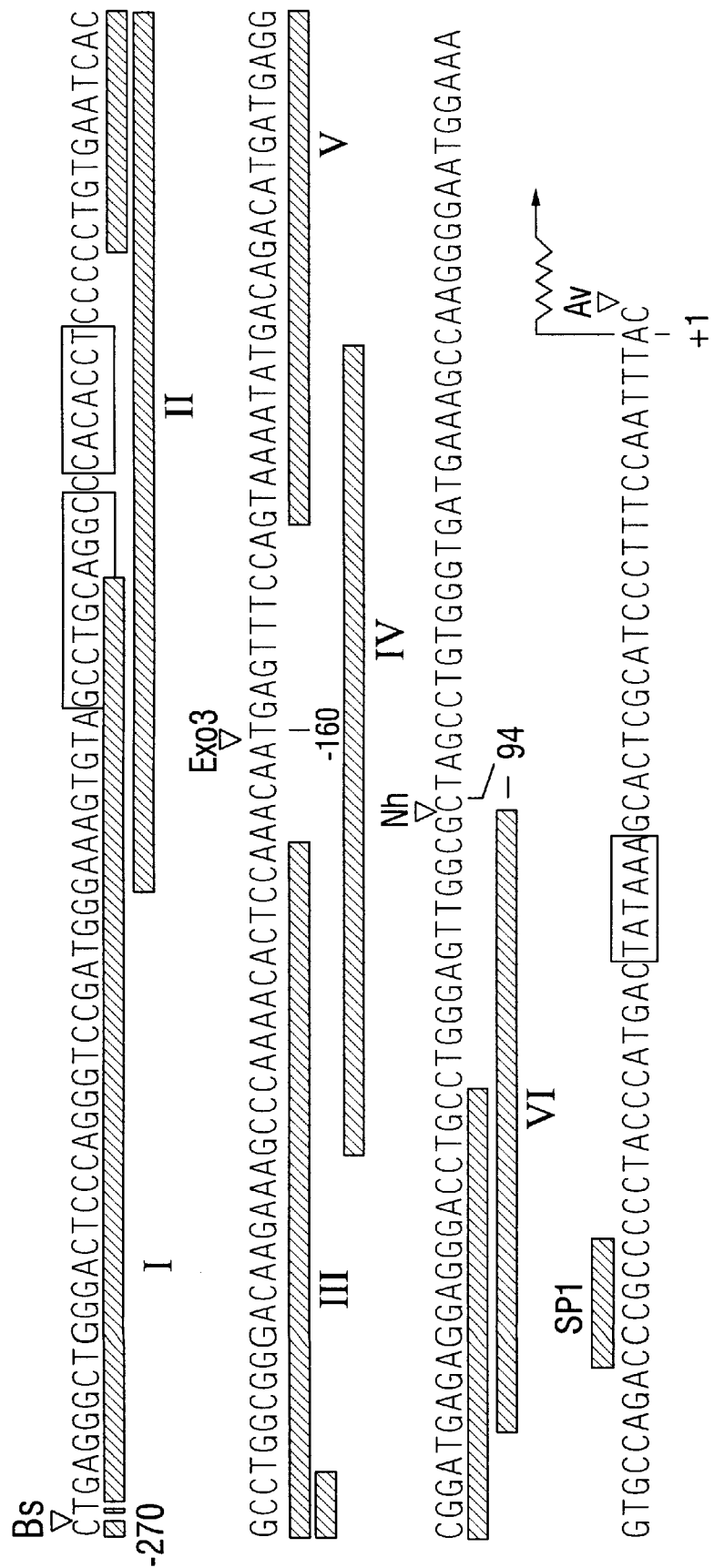

FIG. 5. Nucleotide Sequence of 5' Proximal Domain of the Human K14 Gene (SEQ ID NO:3).

Figure 7A:
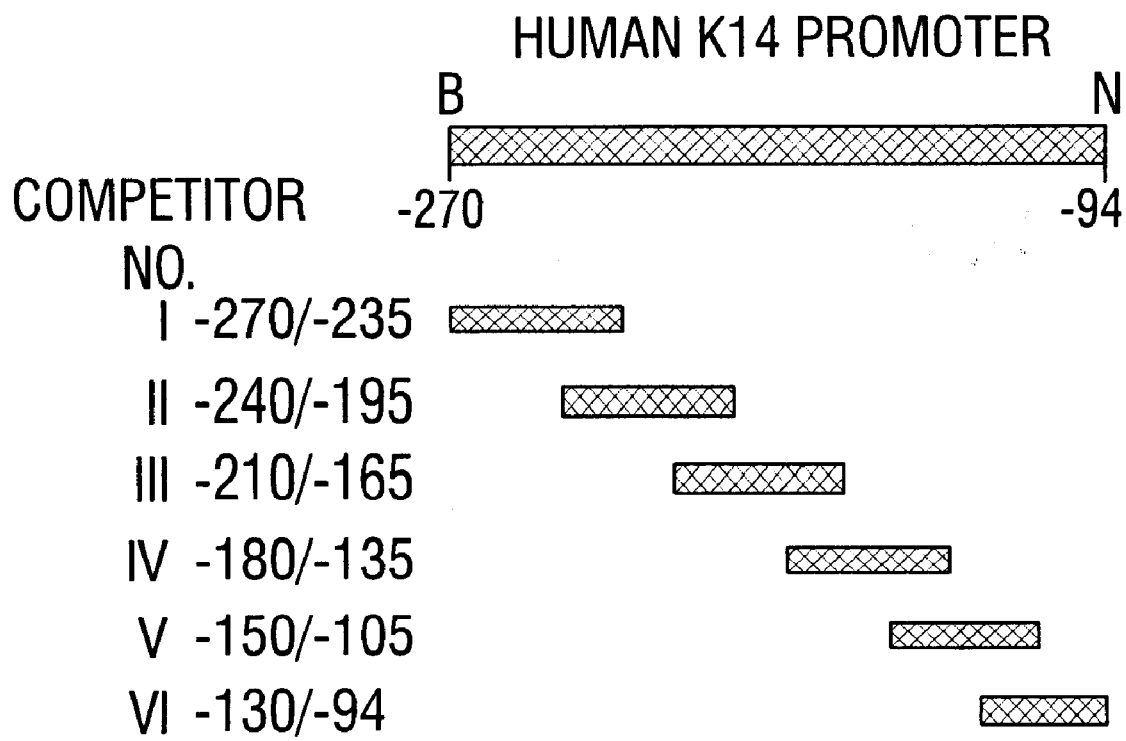
Figure 7B:
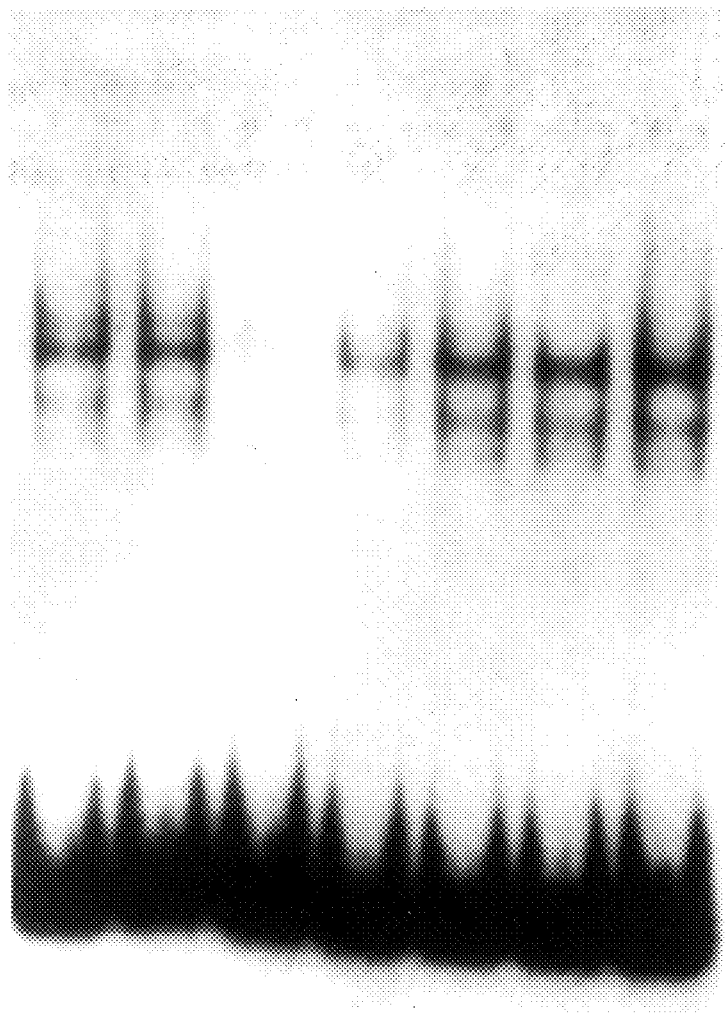

The nucleotide sequence of both strands of the 5' proximal domain was determined (Chen and Seeburg, 1985) (SEQ ID NO:3), and is shown at 72 nucleotides per line. The transcription initiation site was determined previously (Marchuk et al., 1985), and is indicated by the squiggly arrow. Nucleotides are numbered, with this site assigned as +1, and the first nucleotide 5' from this site assigned as -1. Relevant restriction endonuclease sites are indicated with the following abbreviations: Nh, NheI; Av, AvaI; Bs, Bsu36I; Exo3, point of Exonuclease III digestion on the Δ(-160) plasmid. Boundaries of the oligomers used for competition binding studies in FIG. 7A and FIG. 7B are marked by underhead bars and the roman numerals denote the oligomer set number. The TATA box and two sequences described in the text are encased by stippled boxes. Overhead open bar denotes a perfect SP1 consensus site (Wingender, 1988).

Figure 6A:
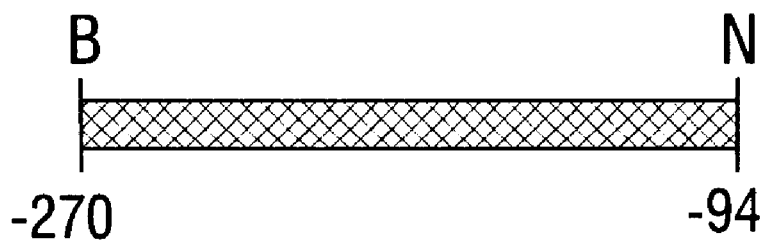
Figure 6A:
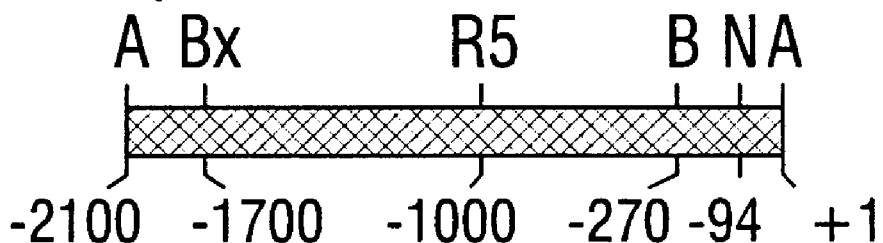
Figures 6B, 6C:
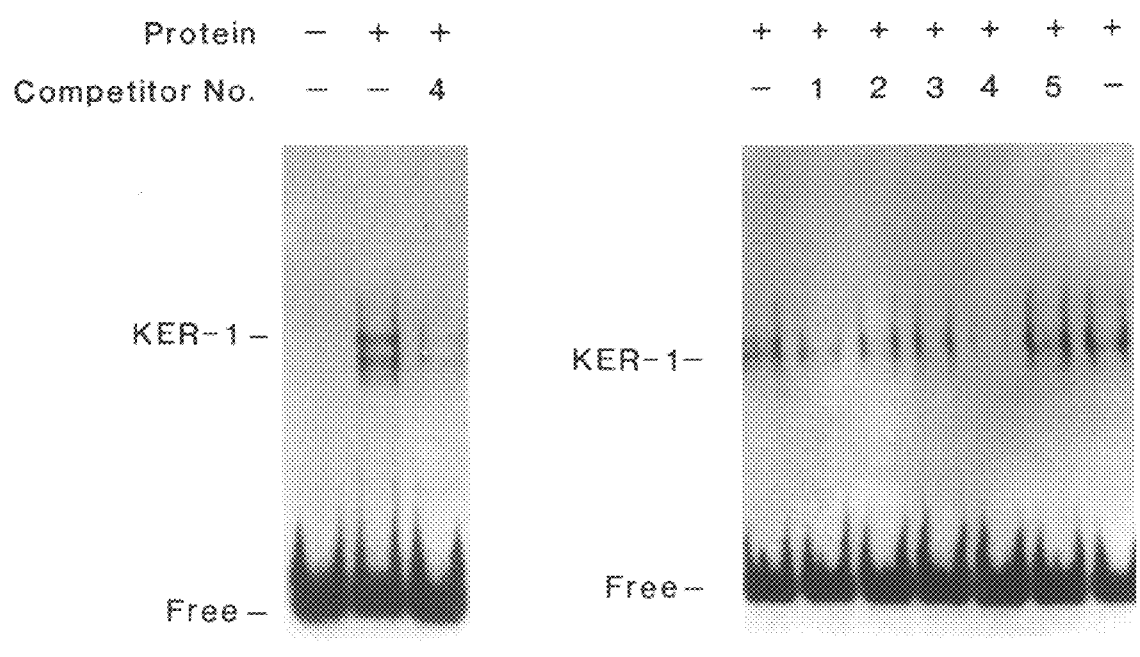

FIG. 6A, FIG. 6B and FIG. 6C. Formation of Specific Keratinocyte Protein Complexes with the Human K14 Proximal Element.

FIG. 6A. Schematic representation of DNA fragments of human K14 promoter used as radiolabeled probe and/or competitors in gel shift assays. Segments used as competitor DNAs are shown below, and were arbitrarily assigned numbers as indicated. Abbreviations for restriction endonuclease sites are: B, Bsu36I; N, NheI; A, AvaI; R5, EcoRV; Bx, BstXI.

FIG. 6B. Gel shift analysis of the proximal regulatory region showing binding activity of KER1 (AP2). Protein-DNA complexes were obtained by combining 5 μg SCC-13 nuclear extract (±protein as indicated over the gel lanes) with 10,000 cpm (~0.5 ng) radiolabeled DNA probe in the presence of an excess of nonspecific competitor (poly dI.dC), or specific competitor (in this case #4, i.e. unlabeled probe DNA as indicated over the gel lanes) as described in the methods section of Example I. Complexes were resolved by electrophoresis through 5% polyacrylamide DNA gels (Maniatis et al., 1989). Gels were exposed to X-ray film for 6 hr. Top arrow at left denotes radiolabeled probe band retarded as a consequence of interaction with a nuclear factor, referred to as KER1 (AP2). Lower arrow denotes free, i.e. uncomplexed, probe. Note that the radiolabeled probe-nuclear factor complex was eliminated by competition with unlabeled competitor #4 DNA.

FIG. 6C. Competition analysis of other K14 5' upstream sequences for the binding of KER1 (AP2) to the proximal element. Competitions were performed with a 100-fold molar excess of unlabeled competitor DNAs. Controls, i.e. radiolabeled probe combined with nuclear extract, but in the absence of competitor DNA are at both ends of the gel. The competitor used in each reaction is indicated over each lane.

FIG. 7A and FIG. 7B. General Localization of KER1 (AP2) Binding Site by Oligomer Competition Studies.

The sequences of one strand of the double stranded oligomers chosen for competition binding studies are shown in FIG. 5, and were assigned roman numerals. overlapping oligomers were selected such that they represented the entire sequence of the K14 proximal domain encompassing nucleotides -270 to -94 probe. The probe was flanked with two restriction sites: Bsu36I (B) and NheI (N). oligomers overlapped each other by 15 bp, such that the internal 15 bp of sequence was unique to a single oligomer set, but the flanking 15 bp of sequence was common to two adjacent oligomer sets. Protein-DNA complexes were formed by combining 5 μg SCC-13 nuclear extract with 10,000 cpm (~0.5 ng) radiolabeled DNA probe corresponding to the complete proximal domain, i.e. nucleotides −270 to −94. Complexes were formed in the presence of a non-specific competitor (poly dI.dC) and as indicated, in the presence of a 100-fold molar excess of unlabeled, double-stranded oligomer as specific competitor. Complexes were resolved and detected as indicated in the legend to FIG. 6A, FIG. 6B and FIG. 6C.

Figures 8A, 8B:
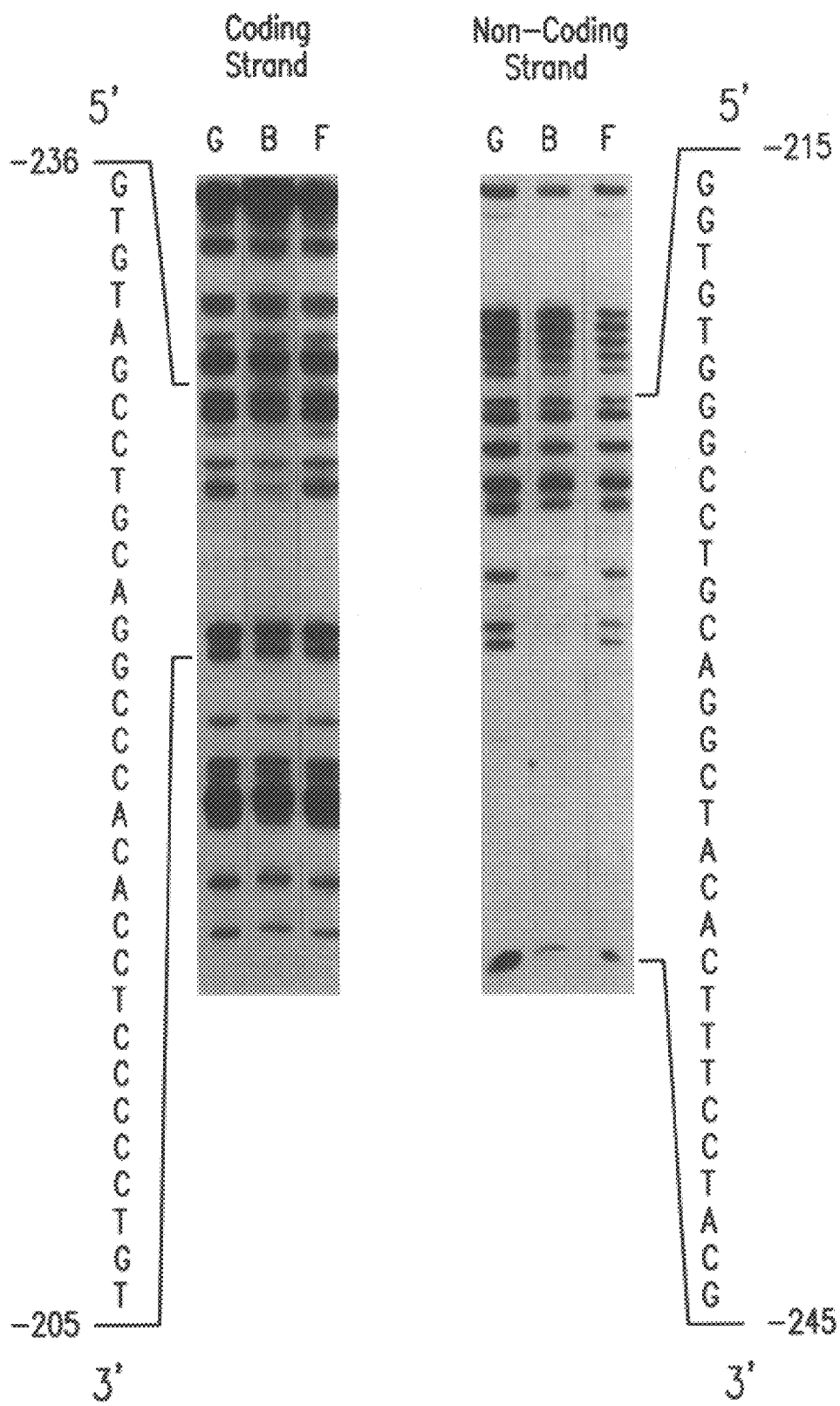

FIG. 8A and FIG. 8B. Methylation Interference Analysis of KER1 (AP2) Binding.

Wild-type probe DNA (−270/−94) was partially methylated with DMS prior to combining with keratinocyte nuclear extract (see Materials and Methods). DNA-protein complexes were separated from free DNA by agarose gel electrophoresis. Complexes were eluted, cleaved with piperidine and analyzed on sequencing gels. Results for the coding and non-coding strands are shown. Lanes: G, partial chemical degradation products of the probe cleaved at guanine residues; B, bound probe DNA; and F, free probe DNA. The solid and open triangles represent G residues that, when methylated, interfered with factor binding strongly or weakly, respectively. The coding strand is shown as 5' GTGTAGCCTGCAGGCCCACACCTCCCCTGT 3' (SEQ ID NO: 16) and the non-coding strand is shown as 5' GGTGTGGGCCTGCAGGCTACACTTTCCTACG 3' (SEQ ID NO: 17).

Figure 9B:
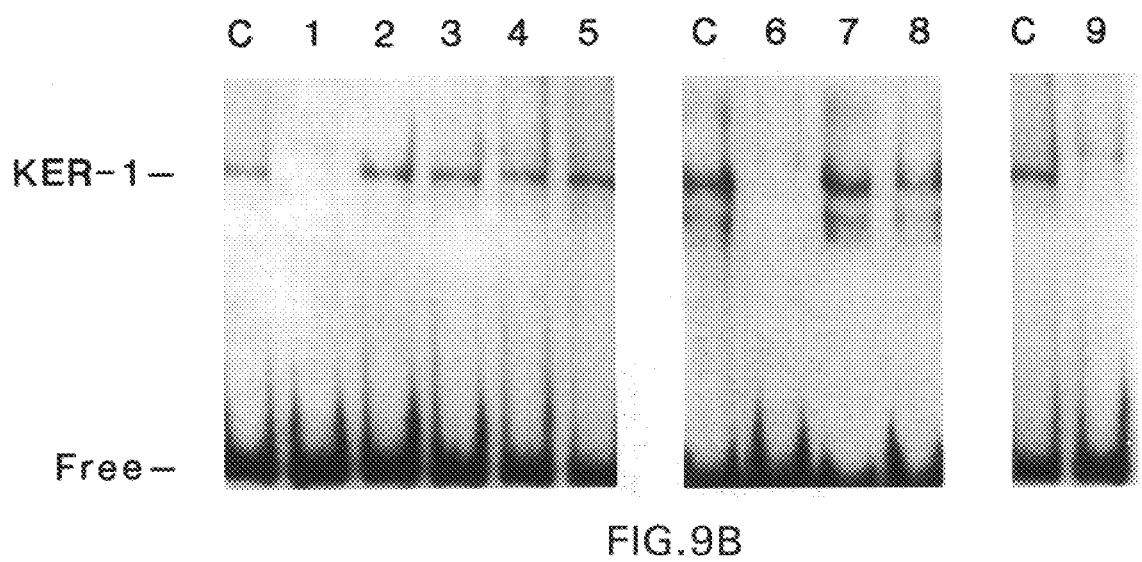

FIG. 9A and FIG. 9B. Mutational Analysis of the KER1 (AP2) Binding Site.

FIG. 9A. Sequences of oligomer sets chosen for more specific competition studies (SEQ ID NO:4 through SEQ ID NO:12, respectively). The boxed sequence represents the putative KER1 (AP2) binding site. The underlined sequences refer to sequences of interest as discussed in the text. Mutated nucleotides are in bold face. The K14 CK 8-mer-like sequence is not a perfect match with the consensus described by Blessing et al. (1987). The K14 wt oligomer corresponds to the wild type sequence of the proximal element as shown in FIG. 6. CEII corresponds to a 38 bp sequence of human papillomavirus (HPV) 11 involved in cell-specific expression of HPV 11 in a cervical carcinoma line C-33A (Chin et al., 1989). The underlined sequence shares 100% identity with the underlined sequence in oligomer K14 wt.

FIG. 9B. Competition binding studies conducted with the annealed oligomers shown above (SEQ ID NO:4 through SEQ ID NO:12, respectively). Studies were conducted as described in the legend to FIG. 6A, FIG. 6B and FIG. 6C. SCC-13 nuclear extracts were combined with the following competitors: lane C, no competitor added; lane 1, K14 wt; lane 2, K14 nut; lane 3, K14 mut (−231); lane 4, K14 mut (−230); lane 5, K14 mut (−229); lane 6 K14 mut (CEII); lane 7, HPV (CEII); lane 8, K14 (CK-8mer); lane 9, K1 (KER1). Note: K1 (KER1) corresponds to a sequence in the 5' upstream sequence of a human K1 gene. This sequence showed 9/10 nucleotide similarity to the putative KER1 (AP2) binding site.

Figure 10:
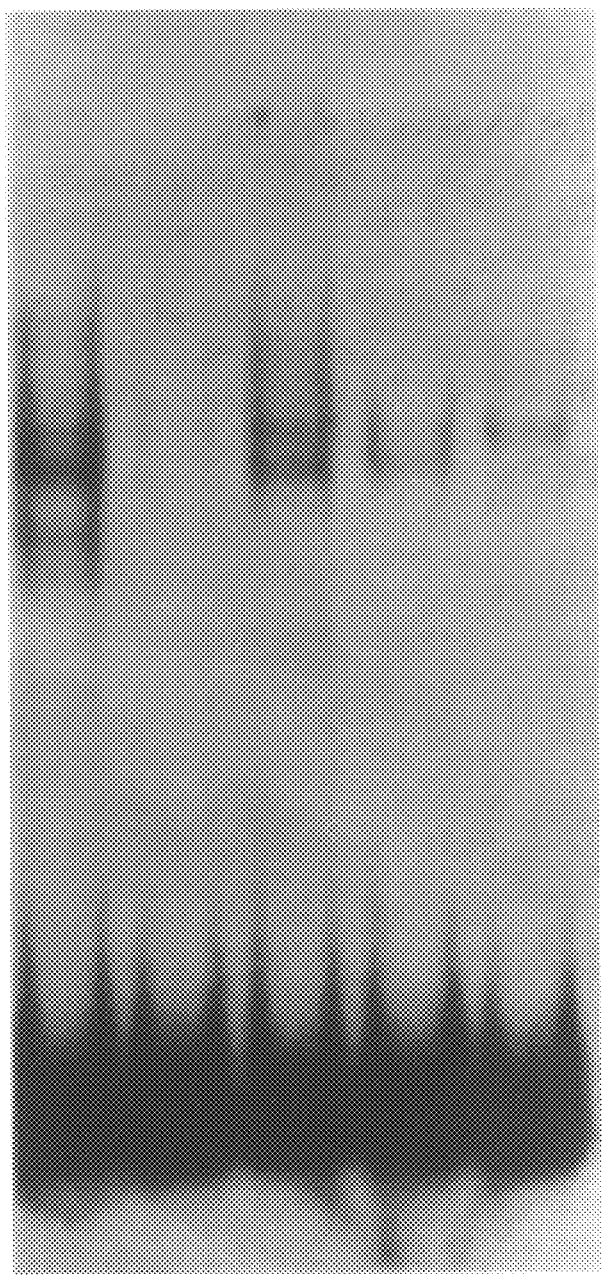

FIG. 10. Examining the Tissue-Specificity of KER1 (AP2) Binding Activity.

Nuclear extracts were isolated from different human cultured cell lines, including: SCC-13 cells from an epidermal squamous cell carcinoma (K14$^+$), WI-38 diploid fibroblasts (K14$^-$), HeLa cells from a cervical adenocarcinoma (K14$^-$), MCF-7 cells from a mammary adenocarcinoma (K14$^-$), and Jurkat lymphoma cells (K14$^-$). Total nuclear protein was measured (Bradford, 1976), and equal amounts (5 μg) from each cell line were combined with 10,000 cpm (~0.5 ng) of $^{32}$P-labeled probe corresponding to the complete proximal element encompassing K14 nucleotides −270 to −94. Complexes were resolved and analyzed as indicated in the legend to FIG. 6A, FIG. 6B and FIG. 6C. Nuclear extracts were from: Lane 1, SCC-13 keratinocytes, lane 2, WI-38 lung fibroblasts, lane 3, HeLa adenocarcinomal cells (simple epithelial), lane 5, MCF 7 mammary adenocarcinoma (simple epithelial), lane 6, Jurkat lymphoma cells.

DETAILED DESCRIPTION OF THE PREFERRED EMBODIMENTS

The present invention embodies the realization that the genetic elements which are responsible for promoting keratinocyte expression can be isolated away from homologous keratinocyte genes and employed to confer keratinocyte expression to associated, typically heterologous, genes.

It is proposed that keratinocyte specific expression is conferred, in part, by a DNA sequence 10 nucleotides in length. Due to its relatively short length, such sequences may be routinely synthesized using DNA synthesizers, thus obviating a need for isolation of the sequences from natural sources.

The inventor has discovered and characterized discreet sequence regions which exist upstream of keratinocyte expressed structural genes. It was found that two regions, termed the proximal and distal elements, are needed to confer keratinocyte regulatory capability. Surprisingly, the minimal sequence requirement, or "core" region, of the proximal element has been localized to the 10 base sequence region G-C-C-T-G-C-A-G-G-C (SEQ ID NO:1). The distal element comprises 300–400 nucleotides which are located 1700 to 2100 nucleotides upstream from the human K14 gene transcriptional start site, i.e. between positions −1700 and −2100. These two elements act co-operatively like an enhancer element and likely serve as binding sites for transcriptional elements.

To obtain a DNA segment containing distal element sequences, one would prepare a DNA segment corresponding to the region located 1700 to 2100 nucleotides upstream from the transcriptional start site of the human K14 gene, i.e. the nucleotides between −1700 and −2100. A convenient method for obtaining such a sequence is to utilize restriction enzyme(s) to excise an appropriate piece of DNA. Restriction enzyme technology is commonly used in the art and will be generally known to the skilled artisan. One would chose any one, or two, of an extensive range of restriction enzymes following an analysis of the sequences broadly around −1700 and −2100 of the K14 gene. The portion of DNA containing the distal site could then be excised using the chosen enzymes. If desired, for example, for subsequent ligation strategies, one could even create a particular restriction site by genetic engineering.

The present invention contemplates that the distal element together with the proximal 10 nucleotide core region can be employed in connection with any selected heterologous or even homologous structural gene. This basic regulatory unit (i.e. the distal element and the 10 nucleotide palindrome) has been characterized from an analysis of upstream control regions of keratinocyte-expressed structural genes. Thus, it will typically be preferred to employ longer sequence stretches that comprise the identified regions. This is because although the core region is all that is ultimately required, it is believed that particular advantages accrue, in terms of regulation and level of induction achieved where one employs sequences which correspond to the natural control regions over longer regions, e.g., up to around 25 or so nucleotides and preferably no longer than 1000 to 1500 or nucleotides in length.

The novel control sequences of the present invention may be even more advantageously employed in the form of multiple units, in numerous various combinations and organizations, in forward or reverse orientations, and the like. Moreover, in the context of multiple unit embodiments and/or in embodiments which incorporate both positive and negative control units, there is not necessarily a requirement that such units be arranged in an adjacent head-to-head or head-to-tail construction in that the improved regulation capability of such multiple units is conferred virtually independent of the location of such multiple sequences with respect to each other. Moreover, there is not necessarily a requirement that each unit comprise the same positive or negative element. All that may be required is that such sequences be located upstream of and sufficiently proximal to a transcription initiation site. However, in a preferred aspect of the improved multiple unit embodiment, the control sequences are located within 200 nucleotides of each other.

When employed in the context of heterologous structural genes, the precise location of the control sequences of the invention with respect to transcription initiation site is not particularly crucial. For example, some benefit will generally be obtained when such control sequences are located up to about 300 nucleotides or more from a transcription initiation site. However, in more preferred embodiments, control sequences are located within 200 nucleotides of such a site.

Therefore, to employ the foregoing regulatory elements in the context of heterologous genes, one simply obtains the structural gene and locates one or more of such control units (proximal and distal elements) upstream of a transcription initiation site. Additionally, a TATA-box sequence is needed upstream of and proximal to a transcription initiation site of the heterologous structural gene. Such sequences may be synthesized and inserted in the same manner as the novel control elements. Alternatively, one may desire to simply employ the TATA sequences normally associated with the heterologous gene. In any event, TATA sequences are most desirably located between about 20 and 30 nucleotides upstream of transcription initiation.

Numerous methods are known in the art for precisely locating selected sequences at selected points within larger sequences. Most conveniently, the desired control sequence or sequences, or combinations of sequences, are synthesized and restriction site linker fragments added to the control sequence termini. This allows for ready insertion of control sequences into compatible restriction sites within upstream regions. Alternatively, synthesized control sequences may be ligated directly to selected regions. Moreover, site specific mutagenesis may be employed to fashion restriction sites into which control sequences may be inserted in the case where no convenient restriction sites are found at a desired insertion site.

However, and as noted above, it is believed that the control sequences of the present invention may be beneficially employed in the context of any heterologous structural gene, with or without additional homologous or heterologous control or promotion sequences.

With respect to the novel screening method for identifying compounds which either stimulate or inhibit keratinocyte gene expression, the method as provided herein preferably employs a reporter gene that confers on its recombinant hosts a readily detectable phenotype that is either expressed or inhibited, as may be the case. Generally reporter genes encode (a) a polypeptide not otherwise produced by the host cell; or (b) a protein or factor produced by the host cell but at lower levels; or (c) a mutant form of a polypeptide produced by the host cell. Preferably the gene encodes an enzyme which produces colorimetric or fluorometric change in the host cell which is detectable by in situ analysis and which is a quantitative or semi-quantitative function of transcriptional activation. Exemplary enzymes include esterases, phosphatases, proteases (tissue plasminogen activator or urokinase) and other enzymes capable of being detected by activity which generates a chromophore or fluorophore as will be known to those of skill in the art.

One such example is *E. coli* beta-galactosidase. This enzyme produces a color change upon cleavage of the indigogenic substrate indolyl-B-D-galactoside by cells bearing beta-galactosidase (Goring et al., 1987; Price et al., 1987, incorporated herein by reference). Thus, this enzyme facilitates automatic plate reader analysis of expression directly in microtiter wells containing transformants treated with candidate activators. Also, since the endogenous beta-galactosidase activity in mammalian cells ordinarily is quite low, the analytic screening system using B-galactosidase is not hampered by host cell background.

Another class of reporter genes which confer detectable characteristics on a host cell are those which encode polypeptides, generally enzymes, which render their transformants resistant against toxins, e.g., the neo gene which protects host cells against toxic levels of the antibiotic G418; a gene encoding dihydrofolate reductase, which confers resistance to methotrexate, or the chloramphenicol acetyltransferase (CAT) gene (Osborne et al., 1985). Genes of this class are not preferred since the phenotype (resistance) does not provide a convenient or rapid quantitative output. Resistance to antibiotic or toxin requires days of culture to confirm, or complex assay procedures if other than a biological determination is to be made.

Other genes for use in the screening assay herein are those capable of transforming hosts to express unique cell surface antigens, e.g., viral env proteins such as HIV gp120 or herpes gD, which are readily detectable by immunoassays. However, antigenic reporters are not preferred because, unlike enzymes, they are not catalytic and thus do not amplify their signals.

The polypeptide products of the reporter gene are secreted, intracellular or, as noted above, membrane bound polypeptides. If the polypeptide is not ordinarily secreted it is fused to a heterologous signal sequence for processing and secretion. In other circumstances the signal is modified in order to remove sequences that interdict secretion. For example, the herpes gD coat protein has been modified by site directed deletion of its transmembrane binding domain, thereby facilitating its secretion (EP 139,417A, incorporated herein by reference). This truncated form of the herpes gD protein is detectable in the culture medium by conventional immunoassays. Preferably, however, the products of the reporter gene are lodged in the intra-cellular or membrane compartments. Then they can be fixed to the culture container, e.g. microtiter wells, in which they are grown, followed by addition of a detectable signal generating substance such as chromogenic substrate for reporter enzymes.

In general, a keratinocyte gene regulator is employed to control transcription and hence influence expression of the reporter gene. The process which in its entirety leads to enhanced transcriptional promoter is termed "activation". The mechanism by which a successful candidate is acting is not material in any case since the objective is to regulate the gene by whatever means will function to do so. While use of the entire keratinocyte upstream promoter will most closely model the therapeutic target, the 10 base regulator region and the distal element of the K14 gene (−1700 to −2100) may optionally be multimerized and placed in front of a TATA box in order to increase the sensitivity of the screening assay.

The keratinocyte promoter and enhancer, whether a hybrid or the native promoter, is ligated to DNA encoding the reporter gene by conventional methods. The elements are obtained by in vitro synthesis and/or recovered from genomic DNA. They are ligated upstream of the start codon of the reporter gene. The promoter also will contain an AT-rich region (TATA box) located between the keratinocyte regulatory elements and the reporter gene start codon. The region 3' to the coding sequence for the reporter gene will contain a transcription termination and polyadenylation site, for example the human keratin K14 polyA site. The promoter and reporter gene are inserted into a replicable vector and transfected into a cloning host such as $E.\ coli$, the host cultured and the replicated vector recovered in order to prepare sufficient quantities of the construction for later transfection into a suitable eukaryotic host.

The host cells used in the screening assay herein generally are mammalian cells, and are either primary or permanent cell lines, or fertilized mammalian embryos. Examples of cultured cells include cultured primary human keratinocytes and SCC-13 keratinocytes derived from a human squamous carcinoma of the skin. Mammalian embryos that may be used include those of the mouse, which would prove useful in transgenic mouse studies. The vector is transfected or microinjected into the desired host, and the reporter gene is assayed for chromosomal integration and or incorporation and expression.

The screening assay may also be conducted by growing the transformants to confluency in microtiter wells, adding serial molar proportions of a candidate substance to a series of wells, and determining the signal level after an incubation period that is sufficient to demonstrate its effect on signal expression. The wells containing varying proportions of candidate are then evaluated for signal activation. Candidates that demonstrate dose related enhancement of reporter gene transcription or expression are then selected for further evaluation as clinical therapeutic agents. The stimulation of transcription may be observed, in which case the candidate compound might be a positive stimulator of the element. Alternatively, the candidate compound might inhibit expression, which would indicate that it functions to oppose the element. Candidate compounds of either class might be useful therapeutic agents.

It should be understood that the screening method herein is useful notwithstanding that effective candidates may not be found, since it would be a practical utility to know that activators or inhibitors do not exist. The invention involves providing a method for screening for such candidates, not in finding them.

EXAMPLE I

A. Methods

1. Construction of Recombinant Clones

I. pK14P(−2300) and Derivatives

Clone pK14P(−2300) was previously referred to as pH3cK14.P (Vassar et al., 1989). In order, it contains ~2300 bp of sequence 5' to the K14 transcriptional initiation site (Marchuk et al., 1985); the 5' untranslated sequence of the K14 gene; the complete human K14 coding sequence except for sequences encoding the 5 carboxy terminal amino acid residues, which were replaced with sequences encoding the antigenic portion of a neuropeptide substance P (Albers and Fuchs, 1987); a TGA translation stop codon; and K14 genomic sequences including the 3' untranslated sequences, polyadenylation signal, and approximately 700 bp of 3' downstream sequence. This insert was cloned into the HindIII and EcoRI sites of plasmid pGEM2 (Promega Biotech., Madison, Wis.) as described by Vassar et al. (1989).

To make 5' deletions of the parent clone pK14P(−2300), convenient restriction endonuclease sites located in the 2300 bp 5' upstream sequence were utilized in conjunction with the unique Eco RI site at the 3' end of the K14 genomic sequences. K14P inserts were created by double digestion with EcoRI and either EcoRV, StuI, HaeII, or AvaI (FIG. 1A) and the inserts cloned into multiple cloning regions of appropriate pGEM plasmids. This resulted in pK14P(−1000), pK14P(−450), pK14P(−94) and pK14(+1), respectively. To create pK14P(−6000), the 6400 bp EcoRI-KpnI fragment was isolated from the 5' end of genomic clone GK-1 (Marchuk et al., 1985), ligated to the 1800 bp KpnI-EcoRI 3' fragment from pK14P(−2300), and inserted into the EcoRI site of pBluescript KS+ (Stratagene). pK14P(−245) and pK14P(−202) were made by limited Bal 31 exonuclease digestion of pK14P(−450), followed by digestion with EcoRI and ligation of the resulting K14P fragment into pGEM2. Finally, pK14P(−2300ΔStu) was created by digesting pK14P(−2300) with StuI and relegating the large fragment.

II. pgK14P(−2300) and Intron-Containing Derivatives

To create pgK14P(−2300) containing introns 1 through 5 from the K14 gene, pK14P(−2300) was partially digested with SphI and completely digested with KpnI. The resulting fragment, containing K14 cDNA sequence from exon 1 through exon 6, was replaced by the corresponding KpnI-SphI sequence from genomic subclone pJgK14 (Giudice and Fuchs, 1987). The KpnI-EcoRI fragment from pgK14P(−2300) containing coding sequences, introns and 3' flanking region, was used to replace the corresponding KpnI-EcoRI fragment from pK14P(−X) clones to create the respective intron-containing clones: pgK14P(−450), pgK14P(−245), pgK14P(−202), pgK14P(−94), pgK14P(+1), and pgK14P(−2300ΔStu). pgK14PI(−6000) was made by ligating the EcoRI-KpnI 5' K14 fragment from pK14P(−6000) with the KpnI-EcoRI 3' K14 fragment from pK14P(−2300) and inserting them into the EcoRI site of pGEM3Z. pK14PI(−2300) was made by replacing the 138 bp KpnI-SacII fragment from pK14P(−2300) with the 1400 bp KpnI-SacII fragment from pgK14PI(−2300) which contains intron I. pK14PV(−2300) was created by replacing the 967 bp BglII fragment from pK14P(−2300) with the 1062 bp fragment from pgK14P(−2300) which contains intron V.

III. K14CAT Expression Vectors: Distal Constructs

To facilitate future cloning steps, the 55 bp HindIII-EcoRI fragment from pGEM3 containing the multiple cloning region was ligated into the HindIII site of pSV0CAT (Gorman et al., 1982) to create pSV0CAT-PL1. Incompatible 5' or 3' extended ends created by restriction enzyme digestion of all DNAs were blunted using $E.\ coli$ polymerase Klenow fragment (5' ends) or T4 DNA polymerase (3' ends). pK14CAT(−2100) was created by inserting the 2100 bp AvaI fragment from pK14P(−2300) into the AvaI site of pSV0CAT-PL1. pK14CAT(−2300) was made by replacing the 1800 bp XbaI-Bsu36I fragment from pk14CAT(−2100) with the 2000 bp HindIII-Bsu36I fragment from pK14P(−2300).

To create pK14CAT(−6000), the 1300 bp XbaI-EcoRV fragment from pK14CAT(−2100) was replaced with the 4700 bp EcoRI-EcoRV fragment from pK14P(−6000). The 1000 bp EcoRV-AvaI fragment from pK14P(−2300) was ligated into the XbaI-AvaI sites of pSV0CAT.PL1 to form pK14CAT(−1000). pK14CAT(−450), pK14CAT(−270) and pK14CAT(−94) were made by digesting pK14CAT(−2100) with StuI and XbaI, Bsu36I and XbaI or NheI and XbaI respectively, and then relegating. Finally, to create pK14CAT(−2000), pK14CAT(−1700) and pK14CAT(−1400), pK14P(−2300) was digested with Bal 31 exonuclease followed by digestion with AvaI. The Bal 31-AvaI fragments were then ligated into the XbaI-AvaI sites of pSV0CAT.PL1.

IV. K14CAT Expression Vectors: Proximal Constructs

The parental construct for proximal deletion plasmids was pK14CAT(−2100). This plasmid was generated by subcloning the 2100 bp AvaI/AvaI fragment of the K14 promoter region into the HindIII site of pSV0CAT after blunting the ends with Klenow fragment. Most internal deletions were made by employing endogenous restriction sites. The other deletions were made first by subcloning the EcoRVINcoI fragment of pK14CAT(−2100) into the multiple cloning region of pGEM 5 (Promega). The resultant subclone was then cut at the BstXI site immediately upstream of the insert (leaving a protected 3' overhang) and at Bsu36I or EcoRV in the insert.

Exonuclease III and mung bean nuclease were then used to generate deletions as described by the manufacturer (New England Biolabs, Mass.). The junctions of the deletion constructs made with this method were sequenced and then subcloned into pK14CAT(−2100). Point mutations of pK14CAT(−2300) were introduced using mutant oligomer hybridization and polymerase chain reactions (PCRs) to generate the appropriate mutant fragments, and then replacing the wild type fragment with the mutant one by subcloning. In all cases, fragments generated by PCR were sequenced to confirm their identity.

2. Cells and Transfections

The human lung fibroblast line WI-38 (ATCC, Rockville, Md.) and human breast adenocarcinoma line MCF-7 (ATCC) were cultured in a 3:1 mixture of Dulbecco's modified Eagle's medium and Ham's F12 medium, supplemented with 10% newborn calf serum. The simple epithelial human cervical carcinoma line HeLa (ATCC) was cultured in the same medium supplemented with 10% fetal calf serum. Human SCC-13 squamous cell carcinoma cells, obtained as a gift from Dr. James G. Rheinwald (Wu and Rheinwald, 1981), were grown in the same medium, supplemented with 10% fetal calf serum, $10^{-10}$M cholera toxin, $10^{-11}$M insulin, $2\times10^{-10}$M triiodothrionine and 5 µg/ml human transferrin (Rheinwald and Green, 1977).

Plasmid DNAs were purified by CsCl density gradient centrifugation as described in Glover (1985). For all transfections, an equal number of SCC-13 keratinocytes were seeded on 100 mm dishes and transfected two days after plating. Plasmid DNAs used for transfections were $6\times10^{-12}$ moles of K14P or CAT expression plasmids, $1.2\times10^{-12}$ moles of pCH110 (Hall et al., 1983) and variable amounts of carrier DNA (pKS$^+$; Stratagene) to equalize the total amount of DNA to ~45 µg/transfection. Transfections were carried out using the calcium phosphate method (Graham and Van der Eb, 1973) followed by a 15% glycerol shock (Parker and Stark, 1979). Cells were harvested 65–90 hours posttransfection for either immunoblot or CAT analysis, and for β-galactosidase analysis.

3. Intermediate Filament Protein Extraction and Immunoblot Analysis

Intermediate filament proteins were isolated according to Wu et al. (1982). The supernatant was removed and frozen (−70° C.) for subsequent analysis of β-galactosidase activity. Protein concentrations were determined by the method of Bradford (1976). IF proteins isolated from equal numbers of transfected cells were resolved using SDS-PAGE, followed by electrophoretic transfer to nitrocellulose plus paper (Micron Separations, Inc., Schiller Park, Ill.) for immunoblot analysis, which was performed as described previously (Albers and Fuchs, 1987). The blot was exposed to X-ray film for 18 hours. The relative levels the substance P-tagged transfected gene product were then estimated by densitometry scanning of autoradiograms.

4. Preparation of Transgenic Mice and Immunohistochemistry of Tissue Sections

DNA inserts from pK14P(−2300), pK14P(−450) and pK14P(−2300ΔStu) were excised, purified, and microinjected into male pronuclei of single cell embryos from an outbred strain (CD-1) of mice (Charles River Laboratories, Inc.) as described previously (Vassar et al., 1989). Mouse tail DNAs were assayed by Southern blot analysis for the presence of human K14P sequences, and gene copy number was estimated (see Vassar et al., 1989). A small piece (~0.25 cm) of tail skin was removed from each transgenic founder mouse, fixed in Bouin's solution and sectioned (5 µm) for immunohistochemistry. The sensitive immunogold enhancement procedure was utilized as described by the manufacturer (Janssen Pharmaceuticals, Piscataway, N.J.). The NCI/34 anti-P antibody was used to detect the K14P transgene product (Accurate Corp., Westbury, N.Y.).

5. Cell Extracts, β-Galactosidase Assays and CAT Assays

Cell extracts were made according to Gorman et al. (1983) and total protein was measured using the Bradford method (1976). CAT protein was measured using the colorimetric sandwich ELISA method as outlined by the manufacturer (5 Prime→3 Prime, Inc., Westchester, Pa.). Briefly, for each sample, equal amounts of extract protein in a total volume of 200 µl of dilution buffer and was added to a microtiter plate well coated with an anti-CAT antibody. After incubation to allow CAT enzyme to bind, and washing steps to reduce non-specific binding, biotinylated anti-CAT antibodies (which detected the bound CAT-antibody complex) were added.

To quantitate the amount of biotinylated anti-CAT antibodies bound to each microtiter well, alkaline phosphatase-conjugated streptavidin was added, and following incubation and washing, p-nitrophenyl phosphate substrate was added. After exactly 30 minutes, the reaction was terminated with NaOH. The resultant color change was then measured at 405 nm using a microtiter plate reader (Molecular Devices, Palo Alto, Calif.). The amount of CAT protein in each extract was estimated using a standard curve generated by assaying a number of standard samples containing various dilutions of purified CAT protein.

For each extract, the number of picograms of CAT protein per microgram of total protein was determined. CAT activity values were compared with samples of extracts from transfections with (a) pSV0CAT, which lacks eukaryotic promoter sequences and thus serves as a baseline indicator of CAT activity, and (b) pK14CAT(−2300) or pKCAT(−2100), as indicated, which of all the K14CAT constructs we made, gave the maximum amount of CAT protein, and were hence taken to represent 100%. Under these conditions, pSV2CAT, containing the SV40 promoter and enhancer (Gorman et al., 1982; 1983), showed an expression level of ~300%.

When two or more extracts were compared, the transfection efficiency of the plasmids was accounted for by comparing the β-galactosidase activities of the extracts and normalizing the CAT values accordingly. The enzymatic assay for β-galactosidase was measured spectrophotometrically following the method described in Glover (1985). For both CAT and β-galactosidase, all assays were performed within the linear range.

6. Nuclear Extracts and Mobility Shift Assays

Nuclear extracts were prepared by the method of Dignam et al. (1983), as modified by Lee et al. (1988). Phenylmethyl sulfonyl fluoride (PMSF) was added to 2 mM in all solutions. Protein concentrations were measured according to Bradford (1976).

For nuclear extract binding studies, double stranded DNA fragments were generated with appropriate restriction endonucleases and resolved by agarose gel electrophoresis. Fragments were recovered by electrophoretic transfer onto DEAE NA45 nitrocellulose (Schleicher and Schuell, Keene, N.H.), followed by visualization of the transferred DNA bands with brief ethidium bromide staining (1 μg/ml) and incubating the filter section containing the desired DNA fragment in the presence of 20 mM Tris, 1 mM EDTA, 1M NaCl, pH 8.0 for 30 minutes at 68° C.

Fragments to be used for probe were radiolabeled using Klenow fragment and $[\alpha$-$^{32}P]dCTP$ (Maniatis et al., 1989). Fragments to be used for competitor were generated either by (a) restriction endonuclease digestion of the K14 5' upstream region and purification as described above, or (b) oligonucleotide synthesis of both strands of a 30–46 bp sequence. oligonucleotides were synthesized using a model 380B DNA synthesizer (Applied Biosystems, Foster City, Calif.). Complementary strands were annealed and purified from single stranded DNAs by gel electrophoresis through 3% Nusieve, 1% Seakem agarose gels (FMC Corporation, Rockland, Md.). DNA fragments were recovered using DEAE NA45 paper, as described above.

Gel shift assays were conducted essentially as described by Fried and Crothers (1981). For each reaction, a nuclear extract mixture was prepared which contained: 5 μg nuclear extract, 5 μg BSA and 2 μg poly dIC.IC (Boeringher Mannheim) in 12% glycerol, 20 mM HEPES-KOH, 75 mM KCl, 2 mM DTT, 2.5 mM $MgCl_2$, 1 mM EDTA, pH 7.9. After a 5 minute preincubation of the mixture on ice, 10,000 cpm (0.5–1.0 ng) of radiolabeled probe, and wherever appropriate a 100-fold molar excess of unlabeled competitor DNA, were added to the mixture. The mixture was then incubated at 30° C. for 20 minutes, followed by quenching briefly on ice. DNA to which protein was bound was then resolved from free DNA by electrophoresis through a 5% non-denaturing polyacrylamide (30:0.8 acrylamide: bisacrylamide) gel, run at 15 mA, 4° C. Before the samples were loaded, the gel was pre-run for at least 90 minutes at 100 V and 4° C. After electrophoresis, gels were dried under vacuum and exposed to X-ray film for 6–12 hrs as indicated in the text.

7. Methylation Interference Analysis

Methylation interference was performed essentially as described (Ausubel et al., 1989). DNA probes were partially methylated with 1 μl DMS for 5 minutes, room temperature. Binding reactions and electrophoresis were as described for the gel mobility shift assay, except 8–10 reactions (20000 cpm probe/assay) were pooled to augment the signals. After electrophoresis, the DNA was located by autoradiography of the wet gel and the bound and free probe were excised from the gel. DNA was recovered by electrophoresing onto DEAE NA45 paper as described above. Carrier tRNA (10 μg) was added, the DNAs were ethanol precipitated and washed with 70% ethanol. Pellets were dissolved in 1M piperidine and incubated for 30 minutes at 90–99° C. As a control, a portion of the original methylated DNA was also treated with piperidine to serve as a marker ladder. After removal of the piperidine by lyophilization, the samples were loaded on 8% polyacrylamide-45% urea gels, which were dried and autoradiographed.

B. Results

1. Sequences Sufficient for Keratinocyte-Specific Expression of the Human K14 Gene Reside in the 5' Upstream Region In the human genome, there are three K14 genes, but only one appears to be functional (Marchuk et al., 1985; Rosenberg et al., 1988). To identify sequences involved in controlling K14 gene expression in keratinocytes, the inventors first investigated whether there might be any important sequences 3' from the transcriptional initiation site. Since keratinocytes transfect with relatively poor efficiency (<1%), an immunological assay was employed to measure the amount of a modified K14 protein produced as a consequence of gene transfection. To distinguish the transgene product from endogenous K14, sequences encoding the C-terminal antigenic portion of substance P were added (Albers and Fuchs, 1987).

A hybrid K14 gene-modified cDNA was then prepared as described in the foregoing Methods section and as outlined in the description for FIG. 1A. Approximately 6000 bp of 5' K14 gene sequence was used to drive expression of the K14P gene, which contained the first five introns out of seven present in the endogenous K14 gene (Marchuk et al., 1985). The construct, referred to as pgK14P(–6000), also contained most of the 3' noncoding sequence of the K14 mRNA and an additional 700 bp of K14 3' downstream sequence. Additional constructs were made which contained 2300 bp of 5' upstream K14 gene sequence coupled to K14P genes with either introns I–V, intron I, intron V or no introns as illustrated in FIG. 1A (see foregoing Methods section for derivation of the constructs).

To examine expression of these constructs in keratinocytes, we transfected them into SCC-13 cells derived from a squamous cell carcinoma of the skin, and known to retain K5 and K14 expression (Wu and Rheinwald, 1981). The transgene product was detected by immunoblot analysis of SDS-PAGE-resolved keratins using an anti-P antibody. The first six lanes of FIG. 1B illustrate the results of transfection analyses of our intron constructs. While the anti-P antibody showed no crossreactivity with any proteins from untransfected keratinocytes (lane 1), cells transfected with any of the five K14P constructs produced an IF protein with mobility slightly greater than 50 kd, as expected for the K14P protein (lanes 2–6). Cells transfected with pgK14P(–6000) produced somewhat lower levels of K14P than cells transfected with any of the constructs containing only 2300 bp of 5' upstream sequence.

While later studies rendered the significance of this observation doubtful, its occurrence prompted the inventors to use the –2300 5' fragment for the intron constructs. Despite occasional variability among repeated assays, cells transfected with any of these intron-containing constructs produced amounts of K14P similar to that made by cells transfected with an intronless construct. Collectively, the data indicated that sequences within the first five introns did not appear to contribute appreciably to K14 gene expression. Additional evidence to support this conclusion is provided below.

2. Role of 5' Upstream Sequences in Human K14 Gene Expression: Preliminary Evidence for the Existence of a Distal Element To examine the role of 5' upstream sequences, either the K14P intronless reporter gene or the K14P reporter gene with five introns was used. These sequences were linked to varying portions of the K14 5' upstream sequences, as shown in FIG. 1A. These constructs were then transfected into SCC-13 keratinocytes and assayed immunologically for K14P protein (FIG. 1B). Surprisingly, none of the constructs containing 1000 bp or less of 5' upstream sequence showed detectable K14P protein as judged by immunoblot analysis (lanes 7–17). This was true whether introns were present (odd numbered lanes) or not (even numbered lanes), and even when the immunoblots were over-exposed, K14P expression was not detected.

To see whether K14P was made in any of the cells transfected with the pK14P($\leq$−1000) constructs, transiently transfected cultures were subjected to immunofluorescence analysis using an anti-P antibody. In fact, a few positive cells could be detected from transfections of all constructs except pK14P(+1), missing the TATA box (data not shown). However, the number of cells showing detectable expression of K14P was ~100× less than that seen for cells transfected with the −2300 constructs.

Interestingly, when sequences 450 bp 5' from the transcription initiation site were coupled with sequences spanning from 1120–2300 bp 5', gene expression was partially restored (lanes 18–19). Thus, immunoblot analysis of IF preparations from cells transfected with pK14P(−2300ΔStu) or pgK14P(−2300ΔStu) showed detectable levels of K14P, which on average were only ~2–5× less than cells transfected with pK14(−2300) [see lanes 18–19, pK14P(−2300ΔStu) and pgK14(−2300ΔStu), respectively]. This observation suggested that within 1180 bp 5' upstream from the transcription initiation site, there is a distal regulatory element(s) necessary for K14 gene expression.

3. Existence of a Distal Regulatory Element in the Human K14 Gene Is Confirmed by Transgenic Mice Studies To verify that the distal element in the human K14 gene was a bona fide requirement for K14 gene expression, the purified genes from pK14P(−2300), pK14P(−450) and pK14P(−2300ΔStu) were introduced into the germline of mouse embryos. Previously, the inventors described analyses of six transgenic mice harboring the insert K14P(−2300) (Vassar et al., 1989). As judged by indirect anti-P immunogold staining of tissue sections from transgenic offspring, every mouse that we tested which was transgenic for the K14P(−2300) construct expressed K14P in stratified squamous epithelial tissues, but not in other tissues (Vassar et al., 1989).

FIG. 2A, FIG. 2B, FIG. 2C, FIG. 2D and FIG. 2E illustrate immunohistochemical anti-P staining of a section (5 μm) of tail skin from a mouse transgenic with ~1–2 copies of the K14P(−2300) construct FIG. 2A. As compared to a control (nontransgenic) mouse tail section FIG. 2B, the transgenic mouse tail showed primarily basal layer staining. In contrast to the easily detectable expression of K14P protein in K14P(−2300) transgenic mice, none of the seven different founder mice harboring 1–10 copies of the K14P (−450) gene showed detectable levels of K14P expression (see FIG. 2C, mouse tail skin from a mouse with 10 copies of the gene). Even though endogenous mouse K14 was readily detectable in these mice, transgene protein was not detected, as judged by both immunohistochemistry and immunoblot analysis. These data are consistent with the in vitro studies showing failure of pK14P(−450) to give detectable levels of expression.

As further confirmation that K14 gene expression requires a distal element, a transgenic founder mouse with ~1–2 copies of K14P(−2300ΔStu) genes showed detectable levels of K14P in skin (see FIG. 2D for tail skin). However, while basal expression was seen in some portions of the tail skin as shown in FIG. 2D, some suprabasal cells also stained with anti-P (FIG. 2E). Despite this somewhat aberrant staining pattern within epidermis, no staining was observed in dermis or in any other non-epidermal cells of the skin. Collectively, the transgenic data are in agreement with the in vitro studies, and indicate that there are sequences distal to the TATA box and transcription initiation site of the K14 gene which are necessary for its expression in stratified squamous epithelia.

4. A More Detailed Analysis of the Distal Element in the Human K14 Gene

To conduct a more extensive and quantitative analyses of the K14 distal element, the sensitivity of the assay was improved by constructing a series of clones in which varying amounts of the 5' upstream sequences of the human K14 gene were used to drive expression of a reporter gene encoding chloramphenicol acetyl transferase (CAT) (Gorman et al., 1983). The 5' deletion clones used for transfection are shown in FIG. 3A.

When SCC-13 cells were co-transfected with a control β-galactosidase plasmid into SCC-13 keratinocytes, and with pK14CAT constructs containing 2000–6000 bp of 5' upstream K14 gene sequence, all transfected cell extracts contained appreciable levels of CAT as measured by the immuno-sandwich ELISA assay (FIG. 3A). When β-galactosidase assays were conducted to correct for variations in transfection efficiencies, it was apparent that within a factor of three, the levels of CAT were similar for cells transfected with either pK14CAT(−6000), pK14CAT(−2300), pK14CAT(−2100) or pK14CAT(−2000) (see relative CAT levels given in FIG. 3A). These data were in agreement with and extended the previous results obtained with K14P constructs.

As expected from the previous K14P studies, we detected only background levels of CAT when SCC-13 cells were transfected with pK14CAT(−1000) or with constructs containing more severe deletions. Moreover, even with cells transfected with a new construct containing 1400 bp of 5' upstream K14 gene sequence, CAT was not above background levels. With another new construct, pK14CAT(−1700), CAT was detected, but at levels which were only ~10% those of cells transfected with a construct containing 300 additional bp of 5' upstream sequence. Collectively, the data indicate that within ~300–400 bp in a region spanning −1700 to −2100 5' upstream from the human K14 gene, there is a sequence which enhances CAT expression in keratinocytes.

5. The Distal Element Contributes to Tissue-specific Expression of the K14 Gene.

To assess whether AP2 is required for tissue-specific expression, the possibility that the K14 distal element (positions −2300 to −1700) might be able to function with a heterologous AP2-less promoter in keratinocytes was tested. The thymidine kinase (TK) promoter-CAT plasmid pBL-CAT2 was chosen for analysis, since this promoter is well-characterized, consisting of binding sites for transcription factor TFIID, Sp1, and "CCAAT box" factors (Luckow & Schutz, 1987). The K14 distal element was inserted 5' upstream from the TX promoter to produce the plasmid pBLDISTCAT. When transfected into SCC13 keratinocytes, pBLDISTCAT elicited CAT expression at a significantly higher level than was obtained with pBLCAT2. Interestingly, pBLDISTCAT-transfected HepG2 cells showed reduced CAT expression over that obtained with pBLCAT2. Thus, as judged from these data, the distal element not only contributed to keratinocyte-specific enhancement of an AP2-less promoter but also seemed to play a role in promoter repression in a nonkeratinocyte (HepG2) cell line. These studies provide the most direct evidence to date that the K14 distal element not only is required for appreciable levels of gene expression but also is involved in tissue specificity.

6. Evidence for a Major Proximal Element Which Acts Cooperatively with the Distal Element to Control Expression of the Human K14 Gene To determine whether any additional sequences are required in conjunction with the distal regulatory element, a series of 5' internal deletions progressing toward the TATA box and transcription initiation site of the K14 gene were constructed. To achieve a measurable CAT signal, sequences −2100 to either −1120 or −1000 were present in all constructs. The clones used for the initial CAT assays are shown in FIG. 3B, along with the relative CAT levels obtained after SCC-13 keratinocytes were cotransfected with each construct and a β-galactosidase control plasmid. For this set of experiments, linear range CAT levels obtained with extracts from cells transfected with pK14CAT (−2100) were taken as 100%. In agreement with the immunological results obtained with the pK14P(−2300ΔStu) construct, appreciable CAT levels (40%±15%) were obtained from extracts of cells transfected with pK14CAT(Δ−1120/−450).

However, since deletion of sequences between the two StuI sites consistently led to somewhat reduced reporter gene expression (either K14P or CAT), there may be a weak positive element(s) located between −450 and −1120 bp. When cells were transfected with pK14CAT(Δ−1120/−270) containing a larger internal deletion, the relative CAT levels obtained were often greater than obtained with the parent construct. Hence, there might be a weak negative regulatory element between −450 and −270 bp. Whenever both sequences were deleted, e.g., in pK14CAT(Δ−1120/−270), transfection yielded SCC-13 extracts with close to wild type K14CAT expression.

Interestingly, removal of an additional 110 bp of K14 gene sequence, to create pK14CAT(Δ−1120/−160), produced a plasmid which when transfected into SCC-13 keratinocytes, generated almost no CAT activity above background levels (FIG. 3B). Further deletion to make pK14CAT(Δ−1120/−94) gave background levels of CAT. These data demonstrated the existence of a major proximal regulatory domain contributing to human K14 gene expression. Without the proximal domain located at −160 to −270, sequences encompassing the distal domain and the TATA box were not sufficient to drive expression of CAT in SCC-13 keratinocytes. Moreover, since constructs containing the proximal domain in the absence of the distal domain are also not able to drive CAT expression in SCC-13 cells (FIG. 3A), these data suggest strongly that the proximal and distal domains act cooperatively to regulate K14 gene expression. A summary of these data is given in FIG. 4.

7. A Protein in SCC-13 Nuclear Extracts Binds to the Proximal Domain

The proximal element was then further characterized. The sequence from −270 to the transcription initiation site was first completed (FIG. 5). At −175 to −183 was located a sequence 5' A A G C C C A A A 3' which was similar to a consensus 5' A A N C C A A A 3' (often referred to as the CK-8 mer) previously recognized by Blessing et al. (1987) to be present in the 5' upstream region of a number of genes expressed primarily in keratinocytes. At −230 to −253 was located the sequence 5' T G G G A A A G 3', which was similar to the SV40 core enhancer consensus 5' G T G G A A A G 3' (see Marchuk et al., 1985). However, the most striking aspect about the sequence within the proximal domain was that the sequence did not share 100% identity with any known regulatory consensus element thus far identified (Wingender, 1988).

To assess whether any of these sequences might be an important part of the proximal element and to determine whether the proximal and distal elements share a common regulatory sequence, the ability of the 110 bp proximal sequence to bind proteins isolated from human keratinocyte (SCC-13) nuclear extracts was examined. The DNA probe was a 176 bp Bsu36 I/NheI fragment, spanning the sequence −270 to −94 bp 5' upstream from the K14 transcription initiation site (FIG. 6A, probe). When radiolabeled double stranded probe was combined with nuclear extract isolated from SCC-13 keratinocytes, a complex was produced which was resolved by non-denaturing acrylamide gel electrophoresis and which showed significantly slower mobility than the probe itself (FIG. 6B, compare first lane, probe alone, with second lane, probe and nuclear extract). Protein-DNA complex formation was not influenced by the presence of non-specific competitor DNA, poly dI.dC (FIG. 6B, all lanes), but was greatly reduced by adding a 100-fold molar excess of specific competitor DNA identical to the radiolabeled probe (FIG. 6B, last lane; FIG. 6C, competitor no. 4). These data suggested that a nuclear factor present in SCC-13 nuclear extracts specifically bound the K14 promoter, within the region of −270 and −94 bp 5' upstream from the transcription initiation site.

When the entire sequence from +1 to −2100 5' upstream of the human K14 gene was divided into 5 DNA fragments (see FIG. 6A for details) and used in 100-fold molar excess as competitors, only the unlabeled fragment containing the −270 to −94 bp sequence competed effectively for binding of probe to the major nuclear factor (FIG. 6C, compare lane with competitor no. 4, i.e. unlabeled probe DNA, with lanes containing competitors no. 1, 2, 3, or 5). These data indicate that the nuclear factor bound specifically to the DNA fragment encompassing the proximal domain, but did not bind effectively to DNA fragments encompassing other 5' upstream K14 sequences, including the DNA fragment encompassing the distal domain. Collectively, the results suggest that if the distal domain binds the same factor as the proximal domain, it probably does so with a weaker association constant.

The major band seen in the gel retardation assays was the only one which was dramatically reduced as a consequence of 100-fold molar excess of unlabeled probe. The protein(s) involved in the formation of this complex were termed KER1 (AP2). Several minor bands were also detected in the gel shift assays (FIGS. 6B and 6C). One band which migrated at slightly slower mobility persisted when the assay was conducted in the presence of unlabeled competitor probe (lanes with competitor no. 4), indicating that this band likely originated from non-specific protein-DNA interactions. Several bands which migrated at slightly faster mobility than the major band were not seen with fresh preparations of nuclear extract and probably represented degradation products of the KER1 (AP2) protein.

8. Localization of the Binding Site for the Keratinocyte Nuclear Factor KER1 (AP2)

To further localize the DNA sequence involved in KER1 (AP2) binding, the mobility shift assays were repeated, this time using annealed (i.e. double stranded) synthetic oligomers as unlabeled competitors. The six sets of complementary oligomers spanned the length of the 176 bp Bsu36I/NheI probe, and each set overlapped the next in sequence by 15 nucleotides (See FIG. 7A). Only the set of oligomers spanning region II (−195 to −240) quantitatively competed for binding of KER1 (AP2) to the 176 bp radiolabeled probe (FIG. 7B, competitor II). The set of oligomers spanning region III (−165 to −210) exhibited some competition for binding, but not consistently. Collectively, the data indicate that the keratinocyte nuclear factor KER1 (AP2) binds to a sequence located within region II. The sequences in oligomer set II were entirely within the sequence extending from −160 to −270, i.e., the sequences shown by CAT assays to constitute the proximal domain necessary for expression of the human K14 gene.

9. KER1 (AP2) Binds to a Specific Sequence in Both the K14 and the K1 Genes and Is Involved in K14 Gene Expression Methylation interference analysis (Ausubel et al., 1989) was used to localize G nucleotides on either strand of the 176 bp Bsu 36I/NheI fragment (−270 to −94) that closely interact with KER1 (AP2). As shown in FIG. 8A for the coding strand, methylation of G residues at positions −231, −224 and −223 (denoted by solid arrowheads) resulted in interference with KER1 (AP2) binding, while methylation of a G residue at position −227 (open arrowhead) showed weaker interference. Similarly, for the noncoding strand, methylation of G residues at positions −230 and −229 interfered with KER1 (AP2) binding, whereas a methylated G residue at position −226 showed weaker interference (FIG. 8B). These data suggested that residues −231 to −222 (encased by a stippled box in FIG. 5) may be involved in KER1 (AP2) binding.

To test the validity of the sequences identified in the methylation interference assays, and to further characterize the KER1 (AP2) binding site, a 47 bp double stranded oligomer with a scrambled 9 bp sequence extending from −231 to −223 in the K14 gene was prepared. This mutant oligomer (competitor no. 2) failed to compete for binding of KER1 (AP2) to the radiolabeled Bsu 36I/NheI fragment (FIG. 9B, lane 2). Three additional double stranded oligomers, with single point mutations in nucleotides −231, −230 and −229, respectively, were also unable to compete for KER1 (AP2) binding (lanes 3–5). Conversely, a double stranded oligomer with four bp mutated outside the putative binding sequence effectively competed for KER1 (AP2) binding (lane 6). These results confirmed and extended the methylation interference data and indicate that the KER1 (AP2) binding site is the sequence 5' G C C T G C A G G C 3' (SEQ ID NO:1). Interestingly, this sequence is a perfect palindrome.

The KER1 (AP2) binding site was adjacent to a 7 bp sequence 5' C A C A C C T 3' (shown encased in a stippled box in FIG. 5) with 100% sequence identity to a sequence found in the E6/E7 promoter element of HPV 11 (Chin et al., 1989). Since a simple epithelial factor, CEII, was shown to bind in the vicinity of this HPV sequence (Chin et al., 1989), it was important to ensure that KER1 (AP2) and its binding site was distinct from CEII and its site. Using gel mobility shift assays, it was demonstrated that mutation of this 7-mer sequence in the K14 gene did not interfere with the ability of a double stranded 45-mer (competitor no. 6) to compete for binding to KER1 (FIG. 9B, lane 6). Similarly, the corresponding HPV 11 sequence (competitor no. 7) did not block binding of KER1 to the wild-type K14 sequence (lane 7). These data confirm that the KER1 (AP2) factor is distinct from the CEII factor. As a final control, the sequence similar to the CK 8-mer, the element found in the 5' upstream region of a number of keratinocyte-specific genes, was shown not compete for KER1 (AP2) binding (FIG. 9B, lane 8).

The sequence 5' G C C T G C A G G C 3' (SEQ ID NO:1) was found only once within the 270 bp proximal domain of the K14 gene. However, the sequence 5' G C C N N N N G G N 3' (SEQ ID NO:13) corresponding to the G nucleotides identified by methylation interference assays, was found three times within this domain. To determine whether this sequence was sufficient to compete for KER1 (AP2) binding, the ability of a 45 bp synthetic oligomer, centered about the sequence 5' G C C T G T G G G 3' (−91 to −83), to compete with the intact proximal region segment was analyzed. Competition was not detected at >100 fold excess. Hence, residues in addition to those identified by methylation interference must be essential for KER1 (AP2) binding.

On searching the 5' upstream sequences of several human keratinocyte genes, some interesting comparisons were found. While 6 bp stretches with 100% identity were found 5' from the involucrin gene (Eckert and Green, 1986) and the K6b gene (Tyner et al., 1985), a sequence identical in 9/10 bp to the KER1 (AP2) binding site, i.e. 5'G G C T G C A G G C 3', (SEQ ID NO:14) was found just 5' from the TATA box in the gene encoding K1, a differentiation-specific gene (Johnson et al., 1985). Interestingly, an oligomer corresponding to the wild-type K1 sequence showed competition for KER1 binding (FIG. 9B, lane 9). This result demonstrated that KER1 (AP2) binds to at least one other mammalian epidermal keratin gene, and suggested the intriguing possibility that the factor may be important in regulating other keratinocyte genes, some of which are expressed in differentiating keratinocytes.

To determine whether the KER1 (AP2) binding site played a functional role in CAT expression, a site-directed mutagenesis was carried out on pK14CAT(−Δ−1120/−270) to engineer a single mutation at residue −230 (C→A). This mutation was chosen because it eliminated competition for KER1 (AP2) binding (see FIG. 9A and FIG. 9B). When the point mutant, pK14CAT (mut −230A) was introduced into SCC-13 cells, the level of CAT expression was reduced to 44% of the wild-type levels, thus demonstrating functionality.

10. KER1 (AP2) Appears to Be More Abundant in Keratinocytes than in Fibroblasts or in Some Simple Epithelial Cell Types To determine whether active KER1 (AP2) is generated by non-keratinocyte cell types, nuclear extracts from a variety of human cell types were isolated: SCC-13, a squamous cell carcinoma cell line of epidermal origin (K14++), diploid WI-38 fibroblasts (K14−−), HeLa, a cervical adenocarcinoma cell line (K14−−), MCF-7, a mammary adenocarcinoma cell line (K14−−), and Jurkat, a T cell lymphoma cell line (K14−−). Relative KER1 (AP2) binding activity was then measured by combining equal amounts of nuclear protein from each cell type with radiolabeled proximal element as probe and repeating the gel shift mobility assays as before. The results of these experiments are shown in FIG. 10.

As judged by this assay, keratinocytes appeared to produce significantly higher levels of KER1 (lane 1) than any of the non-keratinocyte lines (lanes 2–5). While fibroblast (lane 2) and lymphoma extracts (lane 5) showed little or no nuclear binding activity, MCF-7 extracts showed some binding (lane 4), and HeLa extracts showed appreciable binding (lane 3). This finding may explain the substantial promiscuous expression of pK14P and pK14CAT constructs in HeLa cells (see also, Vassar et al., 1989).

11. KER1 is AP2.

It was determined that the last 5 residue of the consensus AP2-binding site were identical to half of the KER1 palindrome. A 26 bp oligomer containing an AP2 site was demonstrated to compete for KER1 binding to the proximal element, suggesting that KER1 may be AP2 or an AP2-like factor. Since a perfect AP2 site is also upstream from the human K5 gene, AP2 could be generally involved in keratinocyte gene expression.

C. Discussion

The Proximal Element: An AP2 binding site.

The foregoing studies revealed the importance of a sequence, 5' G C C T G C A G G C 3', (SEQ ID NO:1) contained within a 110 bp proximal domain 5' from the transcription initiation site of the human K14 gene. That this ten nucleotide motif might be important in regulating keratinocyte-specific gene expression is underscored by the fact that point mutations restrict expression of a reporter CAT gene in transfected keratinocytes and that this sequence is the site for the binding of a nuclear factor, KER1(AP2), which is significantly more abundant in cultured keratinocytes than it is in fibroblasts or in some simple epithelial cell lines. The additional finding that a 45 residue sequence in the human K1 gene competes for KER1 binding suggested that KER1 (AP2) may be involved in the keratinocyte-specific expression of more than one gene.

Interestingly, Snape et al. (1990) reported the characterization of the binding of a Xenopus embryo nuclear factor (KTF-1) to a Xenopus keratin gene expressed specifically at mid-blastula transition in the outer ectoderm. Gel shift and methylation interference assays identified the KTF-1 binding sequence as 5' A C C C T G A G G C T 3', (SEQ ID NO:15) and multiple copies of this sequence linked to a reporter gene resulted in enhancement, albeit non-tissue-specific, of gene expression. With a one nucleotide gap, this Xenopus sequence shared a 10/11 nucleotide sequence identity with the KER1 (AP2) binding site, prompting the present inventors to examine whether the Xenopus and human nuclear factors might be evolutionarily related. Despite the striking sequence similarities between the Xenopus and human sites, the inventors were unable to demonstrate effective competition by a 30 bp oligomer containing the Xenopus sequence (corresponding to "C" in Snape et al., 1990) for binding of KER1 (AP2) to the human K14 proximal element.

Nevertheless, although competition of the Xenopus sequence was not effective against the human sequence, the remarkable similarities in the binding sites and methylation interference patterns of the two nuclear factors are compelling, and suggest the intriguing possibility that the transcription factor KER1 (AP2) may have evolved from KTF-1. That both of these factors appear to be related to, if not identical to, the transcription factor AP2 has been independently demonstrated in the inventor's laboratory (Leask et al., 1991) and by Snape et al., (1991). This is of interest as it has recently been shown that AP2 MRNA is primarily expressed in cells of epidermal and neural lineage (Mitchell et al., 1991) consistent with the differential expression studies by the present inventor (Leask et al., 1990). The Distal Region: Synergistic Effects Between Two Regulatory Regions Within the Human K14 Keratin Gene.

The sequences constituting the distal element have not yet been elucidated, nor have the nuclear factors which might interact with these sequences. However, in preliminary competition experiments, the inventors were unable to demonstrate competition of a fragment containing the distal element for the binding of KER1 (AP2) to the radiolabeled proximal element. While unequivocal demonstration must await elucidation of the precise regulatory sequences of the distal element and the protein(s) that binds to this element, this simplistic data is already suggestive that the two elements may be distinct.

The interdependency upon the distal and proximal regions of the human K14 gene was particularly strong: neither region alone was sufficient to drive expression of a reporter gene coupled to a TATA box and ~75 additional 5' upstream K14 gene sequence, whereas the two regions combined gave marked expression. The most likely interpretation of these data is that the proximal and distal elements and their respective binding proteins act combinatorially with the TATA box and TFIID to create a stable transcription complex. Such synergism has also been reported recently for several promoters, including Drosophila homeobox elements (see for example Han et al., 1989) and the α-skeletal actin regulatory elements (Muscat and Kedes, 1987; Gustafson et al., 1988).

It is interesting to note that the Xenopus keratin gene element, binding KTF-1/AP2 and sharing homologies with the KER1 (AP2) element, was unable to act in single copy to upregulate expression of a reporter gene (Snape et al., 1990). Moreover, in multiple copies, the KTF-1 element was unable to confer epidermis-specific gene expression, suggesting that other factors in addition to KTF-1/AP2 might also be involved in producing high levels of epidermis-specific expression (Snape et al., 1990). As the relation between keratin gene expression in Xenopus embryonic ectoderm and adult human epidermis is more deeply explored, and as other keratinocyte genes are analyzed, the extent to which complex and cooperative regulatory elements are generally utilized in keratinocyte-specific gene expression should become clearer.

Regulation of the Human K14 Gene: Possible Mechanisms for Differentiation-Specific Keratinocyte Expression?

Little is known about the mechanisms controlling the differentiation-specific changes in gene expression patterns in keratinocytes. However, the present finding that a sequence which binds KER1 (AP2) is also found 5' upstream from a human K1 gene is suggestive that at least some regulatory elements found in basal keratinocyte genes might be shared among differentiation-specific keratinocyte genes. Whether changes in gene expression during keratinocyte differentiation are predominantly controlled by transcription factors which might be differentially modified during the keratinization process, or whether transcriptional changes take place via differential expression of new regulatory factors remains to be determined. As more is learned about the distal element involved in K14 gene expression and the role of proximal element factor KER1 (AP2) in the expression of K14 and other keratinocyte-specific genes, some of the remaining mechanisms underlying the changes in gene expression during terminal differentiation may be resolved.

REFERENCES

The following references, as well as those set forth in the specification, are hereby incorporated by reference for the subject matter as specified in the specification and to the extent that they disclose, teach enable or provide a basis for various aspects of the present invention.

Albers, K., and E. Fuchs. 1987. The expression of mutant epidermal keratins CDNAS transfected in simple epithelial and squamous cell carcinoma lines. *J. Cell Biol.* 105: 791–806.

Ausubel, F. M., R. Brent, R. E. Kingston, D. D. Moore, J. A. Smith, J. G. Seidman, and K. Struhl. 1989. Current Protocols in Molecular Biology. John Wiley and Sons, New York, N.Y.

Beaudet. 1985. *Am. J. Hum. Gen.,* 37: 386–406.

Blessing, M., H. Zentgraf, and J. L. Jorcano. 1987. Differentially expressed bovine cytokeratin genes. Analysis of gene linkage and evolutionary conservations of 5'-upstream sequences. *EMBO J.* 6: 567–575.

Blessing, M., J. L. Jorcano, and W. W. Franke. 1989. Enhancer elements directing cell-type-specific expression of cytokeratin genes and changes of the epithelial cytoskeleton by transfections of hybrid cytokeratin genes. *EMBO J* 8: 117–126.

Bradford, M. 1976. A rapid and sensitive method for the quantitation of microgram quantities of protein utilizing the principle of protein dye binding. *Anal. Biochem.* 72: 248–254.

Broker, T. R., and M. Botchan. 1986. Papillomaviruses: Retrospectives and prospectives. *Cancer Cells* 4: 17–36.

Chen, E. Y., and P. H. Seeburg. 1985. Supercoil sequencing: A fast and simple method for sequencing plasmid DNA. *DNA (NY).* 4: 165–170.

Chin, M. T., T. R. Broker and L. T. Chow. 1989. Identification of a novel constitutive enhancer element and an associated binding protein: Implications for human papillomavirus type II enhancer regulation. *J. Virol.* 63: 2967–2976.

Cripe; T. P., T. H. Haugen, J. P. Turk, F. Tabatabai, P. G. Schmid II, M. Durst, L. Gissmann, A. Roman, and L. P. Terek. 1987. Transcriptional regulation of the human papillomavirus-16 E6–E7 promoter by a keratinocyte-dependent enhancer, and by viral E2 trans-activator and repressor gene products: Implications for cervical carcinogenesis. *EMBO J.* 6: 3745–3753.

Dignam, J. D., R. M. Lebowitz, and R. G. Roeder. 1983. Accurate transcription initiation by RNA polymerase II in a soluble extract from isolated mammalian nuclei. *Nucl. Acid. Res.* 11: 1475–1489.

Eckert, R. L., and H. Green. 1986. Structure and evolution of the human involucrin gene. *Cell* 46: 583–589.

Eichner, R., T.-T. Sun, and U. Aebi. 1986. The role of keratin subfamilies and keratin pairs in the formation of human epidermal intermediate filaments. *J. Cell Biol.* 102: 1767–1777.

Fried, M., and D. M. Crothers. 1981. Equilibria and kinetics of lac repressor-operator interactions by polyacrylamide gel electrophoresis. *Nucl. Acid. Res.* 9: 6505–6525.

Fuchs, E., and H. Green. 1980. Changes in keratin gene expression during terminal differentiation of the keratinocyte. *Cell* 19: 1033–1042.

Giudice, G. J., and E. Fuchs. 1987. The transfection of human epidermal keratin genes into fibroblasts and simple epithelial cells: Evidence for inducing a type I keratin by a type II gene. *Cell* 48: 453–463.

Gius, D., S. Grossman, M. A. Bedell, and L. A. Laimins. 1988. Inducible and constitutive enhancer domains in the noncoding region of human papillomavirus type 18. *J. Virol* 62: 665–672.

Glover, D. M. 1985. DNA cloning Vol.2: A practical approach. D. M. Glover (editor) IRL Press, Oxford, United Kingdom.

Goring et al., *Science,* 235:456–458 (1987)

Gorman, C., R. Padmanabhan, B. H. Howard. 1983. High efficiency DNA-mediated transformation of primate cells. *Science* 221: 551–553.

Graham, F. L., and E. van der Eb. 1973. A new technique for the assay of infectivity of human adenovirus 5DNA. *Virology.* 52: 456–467.

Gustafson, T. A., T. Miwa, L. M. Boxer and L. Kedes. 1988. Interaction of nuclear proteins with muscle-specific regulatory sequences of the human cardiac alpha-actin promoter. *Mol. and Cell Bio.* 8: 4110–4119.

Hall, C. V., P. E. Jacob. G. M. Ringold, and F. Lee. 1983. Expression and regulation of *Escherichia coli* lacZ gene fusions in mammalian cells. *J. Mol. Appl. Genet.* 2: 101–109.

Han, K., Levine, M. S., and Manley, J. L. 1989. Synergistic activation and repression of transcription by Drosophila Homeobox proteins. *Cell* 56: 573–583.

Hirochika, H., R. Hirochika, T. R. Broker. and L. T. Chow. 1988. Functional mapping of the human papillomavirus type II transcriptional enhancer and its interactions with the trans-acting E2 proteins. *Genes Devel.* 2: 54–67.

Jiang, C.-K., H. S. Epstein, M. Tomic, I. M. Freedberg, and M. Blumenberg. 1990. Epithelial-specific keratin gene expression: Identification of a 300 base-pair controlling segment. *Nucl. Acids Res.* 18: 247–253.

Johnson, L. D., W. W. Idler, X.-M. Zhou, D. R. Roop, and P. M. Steinert. 1985. Structure of a gene for the human epidermal 67-kDa keratin. *Proc. Natl. Acad. Sci. USA.* 82: 1896–1900.

Kopan, R., and E. Fuchs. 1989. The use of retinoic acid to probe the relation between hyperproliferation-associated keratins and cell proliferation in normal and malignant epidermal cells. *J. Cell Biol.* 109: 295–307.

Leask et al., (1990). *Genes and Development.* 4:1985–1998.

Leask et al., (1991). *Proc. Natl. Acad. Sci.* 88:7948–7952.

Lee, K. A., Bindereif, W. A., and Green, M. R. (1988). A small scale procedure for preparation of nuclear extracts that support efficient transcription and pre-mRNA splicing. *Gene Anal. Tech.* 5: 22–31.

Lersch, R., V. Stellmach, C. Stocks, G. Giudice, and E. Fuchs. 1989. Isolation, sequence, and expression of a human keratin K5 gene: Transcriptional regulation of keratins and insights into pairwise control. *Mol. Cell Biol.* 9: 3685–3697.

Maniatis, T., E. F. Fritsch, and J. Sambrook. 1989. Molecular Cloning: A laboratory Manual. Cold Spring Harbor Press, Nancy Ford (editor).

Marchuk, D., S. McCrohon, and E. Fuchs. 1985. Complete sequence of a type I human keratin gene: Presence of enhancer-like elements in the regulatory region of the gene. *Proc. Natl. Acad. Sci. USA* 82: 1609–1613.

Mitchell et al., (1991). *Genes Dev.* 5:105–119.

Moll, R., W. W. Franke, D. L. Schiller, B. Geiger, and R. Krepler. 1982. The catalog of human cytokeratins: Patterns of expression in normal epithelia, tumors, and cultured cells. *Cell* 31: 11–24.

Muscat, G. E. O., and L. Kedes. 1987. Multiple 5'-flanking regions of the human alpha-skeletal actin gene synergistically modulate muscle-specific expression. *Mol. and Cell Biol.* 7: 4089–4099.

Nelson. W., and T.-T. Sun. 1983. The 50- and 58-kdalton keratin classes as molecular markers for stratified squamous epithelia: Cell culture studies. *J. Cell Biol.* 97: 244–251.

Osborne et al., *Cell,* 42:203–212 (1985)

Parker, B. A., and G. R. Stark. 1979. Regulation of simian virus 40 transcription: Sensitive analysis of the RNA species present early in infections by virus or viral DNA. *J. Virol.* 31: 360–369.

Price et al., Proc. Natl. Acad. Sci. USA, 84:156:156–160 (1987).

Rheinwald, J. G., and H. Green. 1977. Epidermal growth factor and the multiplication of cultured human epidermal keratinocytes. *Nature* 265: 421–424.

Roop, D. R., P. Hawley-Nelson, C. K. Cheng, and S. H. Yuspa. 1983. Keratin gene expression in mouse epidermis and cultured epidermal cells. *Proc. Natl. Acad. Sci. USA* 80: 716–720.

Rosenberg, M., A. RayChaudhury, T. B. Shows, M. M. LeBeau, and E. Fuchs. 1988. A group of type I keratin genes on human chromosome 17: characterization and expression. *Mol. and Cell Biol.* 8: 722–736.

Snape, A. M., Jonas, E. A., and Sargent, T. D. 1990. KTF-1, a transcriptional activator of Xenopus embryonic keratin expression. *Development* 109: 157–165.

Snape et al., (1991) *Development* 109: 157–165.

Stellmach, V. M., and E. Fuchs. 1989. Exploring the mechanisms underlying cell type-specific and retinoid-mediated expression of keratins. *The New Biologist* 1: 305–317.

Sun, T.-T., R. Eichner, A. Schermer, D. Cooper, W. G. Nelson, and R. A. Weiss. 1984. Classification, expression, and possible mechanisms of evolution of mammalian epithelial keratins: a unifying model. In *The Cancer Cell*. Vol. 1. *The transformed phenotype*. (ed. A. Levine, W. Topp. G. van de Woude, and J. D. Watson), pp. 169–176. Cold Spring Harbor Laboratory, Cold Spring Harbor, New York.

Swift, F. V., K. Bhat, H. B. Younghusband, and H. Hamada. 1987. Characterization of a cell type-specific enhancer found in the human papilloma virus type 18 genome. *EMBO J.* 6: 1339–1344.

Tyner, A. L., Eichman, M. J., and Fuchs, E. (1985). The sequence of a type II keratin gene expressed in human skin: conservation of structure among all intermediate filament genes. *Proc. Natl. Acad. Sci. USA* 82: 4683–4687.

Vassar, R., M. Rosenberg, S. Ross, A. Tyner, and E. Fuchs. 1989. Tissue-specific and differentiation-specific expression of a human K14 keratin gene in transgenic mice. *Proc. Natl. Acad. Sci. USA* 86: 1563–1567.

Watt, F. M. 1988. The epidermal keratinocyte. *BioEssays* 8: 163–167.

Wingender, E. 1988. Compilation of transcription regulating proteins. *Nucleic Acids Res.* 16: 1879–1902.

Wu, Y.-J., and J. G. Rheinwald. 1981. A new small (40 kd) keratin filament protein made by some cultured human squamous cell carcinoma. *Cell* 25: 627–635.

Wu, Y.-J., L. M. Parker, N. E. Binder, M. A. Beckett, J. H. Sinard, C. T. Griffiths, and J. G. Rheinwald. 1982. The mesothelial kertains: A new family of cytoskeleton proteins identified in cultured mesothelial cells and nonkeratinizing epithelia. *Cell* 31: 693–703.

---

What is claimed is:

1. A segment of DNA of up to 2100 nucleotides in length and comprising functionally translocatable keratinocyte gene regulatory distal and proximal elements from the human K14 gene, provided that said segment is free of the structural gene ordinarily under the transcriptional control of said regulatory elements, wherein
   (a) the proximal element comprises the nucleotide sequence: 5'-G-C-C-T-G-C-A-G-G-C-3' and a TATA box; and
   (b) the distal element encompasses nucleotides −1700 to −2100 of the human K14 gene contained in plasmid pGK14P.

2. The DNA segment of claim 1, defined further as a segment of up to 500 nucleotides in length.

3. A method for expressing a polypeptide in a recombinant host cell comprising:
   (a) preparing a first DNA segment as defined by claim 1;
   (b) constructing a second DNA segment by positioning said first DNA segment upstream from and proximal to a transcription initiation site of a selected structural gene encoding the polypeptide such that said structural gene is under the transcriptional control of the keratinocyte gene regulatory elements of said first DNA segment;
   (c) transforming said host cell with said second DNA segment; and
   (d) culturing the transformed host cell to express the polypeptide.

4. The DNA segment of claim 1, further defined as −1 to −2100 of the human K14 gene.

5. A DNA molecule comprising functionally translocatable keratinocyte gene regulatory distal and proximal elements from the human K14 gene in combination with a structural gene not ordinarily under the transcriptional control of said elements, wherein
   (a) the proximal element comprises the nucleotide sequence: 5'-G-C-C-T-G-C-A-G-G-C-3' and a TATA box; and
   (b) the distal element encompasses nucleotides −1700 to −2100 of the human K14 gene contained in plasmid pGK14P;
and further wherein said structural gene and regulatory elements are combined in a manner such that said structural gene is under the transcriptional control of said regulatory elements.

6. The DNA molecule of claim 5, wherein the structural gene is a marker gene.

7. The DNA molecule of claim 5, wherein the proximal and distal regulatory elements are further defined as −1 to −2100 of the human K14 gene.

8. The method of claim 3, wherein the structural gene is a marker gene.

9. A recombinant DNA vector comprising a DNA segment as defined by any one of claims 1, 2 or 6–7.

10. A recombinant cell comprising a recombinant DNA vector as defined by claim 9.

11. A recombinant DNA vector comprising a DNA molecule as defined by any one of claims 5 or 8.

12. The recombinant cell of claim 8, wherein said cell is a mammalian cell.

13. The method of claim 3, wherein said host cell is a mammalian cell.

14. The recombinant cell of claim 12, wherein said cell is a keratinocyte.

15. The method of claim 13, wherein said host cell is a keratinocyte.

16. A segment of DNA comprising functionally translocatable keratinocyte gene regulatory distal and proximal elements from the human K14 gene, provided that said segment is free of the structural gene ordinarily under the transcriptional control of said regulatory elements, wherein:
  (a) the proximal element comprises the nucleotide sequence: 5'-G-C-C-T-G-C-A-G-G-C-3' and a TATA box; and
  (b) the distal element encompasses nucleotides −1700 to −2100 of the human K14 gene contained in plasmid pGK14P.

17. A DNA molecule comprising functionally translocatable keratinocyte gene regulatory distal and proximal elements from the human K14 gene in combination with a structural gene not ordinarily under the transcriptional control of said elements, wherein:
  (a) the proximal element comprises the nucleotide sequence: 5'-G-C-C-T-G-C-A-G-G-C-3' and a TATA box; and
  (b) the distal element encompasses nucleotides −1700 to −2100 of the human K14 gene contained in plasmid pGK14P;

and further wherein said structural gene and regulatory elements are combined in a manner such that said structural gene is under the transcriptional control of said regulatory elements.

* * * * *

UNITED STATES PATENT AND TRADEMARK OFFICE
CERTIFICATE OF CORRECTION

PATENT NO. : 6,183,984 B1  Page 1 of 1
DATED : February 6, 2001
INVENTOR(S) : Fuchs It is certified that error appears in the above-identified patent and that said Letters Patent is hereby corrected as shown below:

<u>Title page,</u>
Item [54], after "SEQUENCES" delete "FOR PROMOTING" and replace with
-- CONFERRING -- therefor.
Item [74], delete "Arnold White & Durkee" and replace with
-- Fulbright and Jaworski, L.L.P. -- therefor.

<u>Column 36,</u>
Line 57, after "1, 2" insert -- 4 -- therefor.
Line 62, after "claim", delete "8" and insert -- 10 -- therefor.

Signed and Sealed this

Twenty-fifth Day of February, 2003

JAMES E. ROGAN
*Director of the United States Patent and Trademark Office*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:1:

GCCTGCAGGC    10

(2) INFORMATION FOR SEQ ID NO:2:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:2:

TGCAGGTGTG A    11

(2) INFORMATION FOR SEQ ID NO:3:

(i) SEQUENCE CHARACTERISTICS:
        (A) LENGTH: 273 base pairs
        (B) TYPE: nucleic acid
        (C) STRANDEDNESS: single
        (D) TOPOLOGY: linear (xi) SEQUENCE DESCRIPTION: SEQ ID NO:3:

```
CTGAGGGCTG GGACTCCCAG GGTCCGATGG GAAAGTGTAG CCTGCAGGCC CACACCTCCC      60

GTGTGAATCA CGCCTGGCGG GACAAGAAAG CCCAAAACAC TCCAAACAAT GAGTTTCCAG     120

TAAAATATGA CAGACATGAT GAGGCGGATG AGAGGAGGGA CCTGCCTGGG AGTTGGCGCT     180
```

| AGCCTGTGGG TGATGAAAGC CAAGGGGAAT GGAAAGTGCC AGACCCGCCC CCTACCCATG | 240 |
| ACTATAAAGC ACTCGCATCC CTTTCCAATT TAC | 273 |

(2) INFORMATION FOR SEQ ID NO:4:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:4:

| GTGGAAAGTG TAGCCTGCAG GCCCACACCT CCCCCTGTAA TCACGCCG | 48 |

(2) INFORMATION FOR SEQ ID NO:5:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:5:

| GTGGAAAGTG TATAGGATCC ACCCACACCT CCCCCTGTAA TCACGCCG | 48 |

(2) INFORMATION FOR SEQ ID NO:6:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:6:

| GTGGAAAGTG TATCCTGCAG GCCCACACCT CCCCCTGTAA TCACGCCG | 48 |

(2) INFORMATION FOR SEQ ID NO:7:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:7:

| GTGGAAAGTG TAGACTGCAG GCCCACACCT CCCCCTGTAA TCACGCCG | 48 |

(2) INFORMATION FOR SEQ ID NO:8:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:8:

| GTGGAAAGTG TAGCATGCAG GCCCACACCT CCCCCTGTAA TCACGCCG | 48 |

(2) INFORMATION FOR SEQ ID NO:9:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:9:

GTGGAAAGTG TAGCCTGCAG GCAGCTACCT CCCCCTGTAA TCACGCCG                48

(2) INFORMATION FOR SEQ ID NO:10:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:10:

TGCCAACAAC ACACCTGGCG CCAGGGCGCG GTATTGC                            37

(2) INFORMATION FOR SEQ ID NO:11:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:11:

TGGCGGGACA AGAAAGCCCA AAACACTCCA AACAATG                            37

(2) INFORMATION FOR SEQ ID NO:12:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:12:

CGTAAAAATC TTGTATGGCT GCAGGCAAGC CAAACCCTTG AC                      42

(2) INFORMATION FOR SEQ ID NO:13:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 4..10
        (D) OTHER INFORMATION: /mod_base= OTHER
            /note= "N = A or G or C or T"

(xi) SEQUENCE DESCRIPTION: SEQ ID NO:13:

GCCNNNNGGN                                                         10

(2) INFORMATION FOR SEQ ID NO:14:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:14:

GGCTGCAGGC                                                         10

-continued (2) INFORMATION FOR SEQ ID NO:15:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (xi) SEQUENCE DESCRIPTION: SEQ ID NO:15:

ACCCTGAGGC T                                                11

(2) INFORMATION FOR SEQ ID NO:16:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:16:

GTGTAGCCTG CAGGCCCACA CCTCCCCCTG T                31

(2) INFORMATION FOR SEQ ID NO:17:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:17:

GGTGTGGGCC TGCAGGCTAC ACTTTCCTAC G                31